US012765746B2

(12) United States Patent
Park et al.

(10) Patent No.: US 12,765,746 B2
(45) Date of Patent: Oct. 20, 2026

(54) SHOES CARE DEVICE

(71) Applicant: LG ELECTRONICS INC., Seoul (KR)

(72) Inventors: Ji Hun Park, Seoul (KR); Ji Hun Kim, Seoul (KR); Yeon A Na, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 295 days.

(21) Appl. No.: 18/719,470

(22) PCT Filed: Dec. 8, 2022

(86) PCT No.: PCT/KR2022/019924
§ 371 (c)(1),
(2) Date: Jun. 13, 2024

(87) PCT Pub. No.: WO2023/113380
PCT Pub. Date: Jun. 22, 2023

(65) Prior Publication Data

US 2025/0064294 A1 Feb. 27, 2025

(30) Foreign Application Priority Data

Dec. 17, 2021 (KR) ........................ 10-2021-0182033

(51) Int. Cl.
*A47L 23/20* (2006.01)
*A47L 23/02* (2006.01)
*A61L 2/07* (2006.01)

(52) U.S. Cl.
CPC ............. *A47L 23/205* (2013.01); *A47L 23/02* (2013.01); *A61L 2/07* (2013.01); *A47L 2601/04* (2013.01);
(Continued)

(58) Field of Classification Search
CPC ........ A47L 23/205; A47L 23/20; A47L 23/02; A47L 2601/04; A61L 2/07; A61L 2202/11; A61L 2202/121; A61L 2202/122
See application file for complete search history.

(56) References Cited

U.S. PATENT DOCUMENTS 5,016,364 A * 5/1991 Cochrane ................ A47L 23/20
34/195
11,408,679 B2 * 8/2022 Ohnari .................... A47L 23/20
(Continued)

FOREIGN PATENT DOCUMENTS

JP 9-108495 A 4/1997
JP 2001-227863 A 8/2001
(Continued)

*Primary Examiner* — Eret C Mcnichols
(74) *Attorney, Agent, or Firm* — Birch, Stewart, Kolasch & Birch, LLP

(57) ABSTRACT

A shoe care device include an accommodation space configured to accommodate shoes; a connection path constituting a flow path; a blowing part disposed in the connection path and configured to blow the air; a dehumidifying part disposed in the connection path and configured to dehumidify the air; a heating part disposed in the connection path to heat the air; a regeneration path branching from the connection path and configured such that the air heated by the heating path moves therethrough; a sump configured to accommodate water condensed inside the shoe care device; and a drain tank configured to store water drained from the sump. The drain tank includes: a first drain inlet hole provided at the upper end of the drain tank; and a first water level limit hole provided in the lower portion of the first drain inlet hole and connected to the sump.

20 Claims, 22 Drawing Sheets

(52) U.S. Cl.
CPC ...... *A61L 2202/11* (2013.01); *A61L 2202/121* (2013.01); *A61L 2202/122* (2013.01)

(56) References Cited

U.S. PATENT DOCUMENTS

| | | | | |
|---|---|---|---|---|
| 11,591,746 | B2 * | 2/2023 | Woo | D06F 58/203 |
| 12,232,683 | B2 * | 2/2025 | Jung | A47L 23/205 |
| 12,256,881 | B2 * | 3/2025 | Lee | A47L 23/205 |
| 12,359,364 | B2 * | 7/2025 | Jang | A61L 2/10 |
| 12,414,673 | B2 * | 9/2025 | Kim | A47L 23/205 |
| 2019/0387955 | A1 | 12/2019 | Lassonde | |
| 2021/0401260 | A1 * | 12/2021 | Youn | A47L 23/02 |
| 2022/0233731 | A1 * | 7/2022 | Chang | A61L 2/10 |
| 2024/0148230 | A1 * | 5/2024 | Kim | A47L 23/205 |
| 2024/0156323 | A1 * | 5/2024 | Ban | A47L 23/205 |
| 2024/0156324 | A1 * | 5/2024 | Kim | A47L 23/205 |
| 2024/0260810 | A1 * | 8/2024 | Kim | A47L 23/205 |
| 2024/0344767 | A1 * | 10/2024 | Kim | A47B 61/04 |
| 2025/0098936 | A1 * | 3/2025 | Kim | A47L 23/205 |
| 2025/0235077 | A1 * | 7/2025 | Kim | A47L 23/205 |
| 2025/0325165 | A1 * | 10/2025 | Kim | A47L 23/205 |
| 2025/0359725 | A1 * | 11/2025 | Kim | A47L 23/205 |

FOREIGN PATENT DOCUMENTS

| | | | |
|---|---|---|---|
| JP | 2005-230324 | A | 9/2005 |
| KR | 10-2000-0009653 | A | 2/2000 |
| KR | 10-0941521 | B1 | 2/2010 |
| KR | 10-1004826 | B1 | 12/2010 |
| KR | 10-1037245 | B1 | 5/2011 |
| KR | 10-1173213 | B1 | 8/2012 |
| KR | 10-2015-0118796 | A | 10/2015 |
| KR | 10-2020-0030404 | A | 3/2020 |
| KR | 10-2020-0142840 | A | 12/2020 |
| KR | 10-2021-0030856 | A | 3/2021 |
| WO | WO 2020/055024 | A1 | 3/2020 |

* cited by examiner

SHOES CARE DEVICE

CROSS REFERENCE TO RELATED APPLICATIONS

This application is the National Phase of PCT International Application No. PCT/KR2022/019924, filed on Dec. 8, 2022, which claims priority under 35 U.S.C. 119(a) to Patent Application No. 10-2021-0182033, filed in the Republic of Korea on Dec. 17, 2021, all of which are hereby expressly incorporated by reference into the present application.

TECHNICAL FIELD

The present invention relates to a shoes care device, and more particularly, to a shoes care device which treats shoes by air circulation.

BACKGROUND

Shoes may get wet by a wearer's sweat, external contaminants, or rain or snow. Wearing such shoes may make the wearer uncomfortable, and in this condition, germs may also breed or the shoes may stink.

Accordingly, there is an increasing interest in a shoes care device, which removes germs and odors by performing a predetermined treatment on the shoes so that a user can comfortably wear the shoes all the time.

For the shoes care device, Korean Patent No. 10-1037245 (hereinafter, referred to as "Prior Art Document 1"), entitled, "Apparatus for sterilization disposal of shoes", includes a main body, an ultraviolet emission module, and a deodorization module.

According to Prior Art Document 1 above, the shoes are disposed in a sterilization chamber of the main body, and the ultraviolet emission module is driven to remove germs and odors of the shoes. Furthermore, the air in the sterilization chamber is sucked into a ventilation pipe and discharged to the outside of the main body through an exhaust port through the deodorization module.

Here, the deodorization module includes a deodorization column made up of materials such as zeolite, activated carbon, and charcoal, and removes contaminants from the air discharged from the inside of the main body to the outside by the deodorization column.

According to Prior Art Document 1 above, the air from which moisture has been removed by a deodorization module including zeolite and activated carbon can be discharged to the outside of the apparatus for sterilization of shoes.

However, in Prior Art Document 1 above, since the air is discharged to the outside of the apparatus for sterilization of shoes, the air that has not sufficiently removed moisture or odors may be discharged to the outside of the apparatus for sterilization of shoes, and such air may be discharged to the inside where the wearer resides.

In addition, Korean Patent Unexamined Publication No. 10-2000-0009653 (hereinafter referred to as "Prior Art Document 2"), entitled, "The shoes cabinet for sanitation", discloses a shoe closet that includes a main body, a far infrared radiation part, a circulation fan, an air circulation passage, and a sanitary filter portion.

According to Prior Art Document 2 above, while storing shoes in the shoe closet, hygiene treatments such as dehumidification, sterilization, and deodorization can be performed on the shoes by far-infrared rays and a filter during the storing of the shoes.

Here, since the sanitary filter portion is filled with excellent adsorptive materials such as charcoal, it can serve to adsorb moisture in the process of ventilating air and filter bacteria, as well as to capture malodorous substances.

According to Prior Art Document 2 above, the air is circulated by a circulating fan in a shoe closet, and the sanitary filter portion is disposed on a circulation path of the air to remove germs and odors in the air.

However, since Prior Art Document 2 above does not consider a technology to prevent the reduction of the performance of the sanitary filter portion configured to remove moisture or odors, a user may not be satisfied because the shoes are not properly treated at the time of using a shoes care device.

As described above, for the shoes care device that removes germs or odors by treating the shoes in a predetermined manner, a task that has to be solved to ensure proper performance for shoes treatment while preventing the air used for dehumidification and deodorization from being exposed to the user is present in in the process of treating the shoes.

However, there is a limitation in that the conventional shoes care device cannot properly solve such a task.

In addition, when designing and manufacturing devices including a dehumidifier such as zeolite, it is necessary to consider how the dehumidification efficiency of a dehumidifying material can be further improved, whether the dehumidifying material can be effectively regenerated, whether water vapor generated during the use of the shoes care device and the regeneration of the dehumidifying material can be effectively removed or managed, whether moisture is left in an unintended area during use of the shoes care device and the regeneration of the dehumidifying, whether components are properly disposed in a limited space, and whether the devices provides excellent use convenience. There is a need to develop a shoes care device that takes these matters into consideration.

In addition, the reduction of manufacturing costs, the convenience of manufacturing and assembling each component, and the convenience of maintenance needs to be considered in the development of the shoes care device.

DISCLOSURE

Technical Problem

An object to be achieved by the present invention is to solve the aforementioned problems caused by a shoes care device which treats shoes by air circulation.

Specifically, an object to be achieved by the present invention is to provide a shoes care device which can ensure proper performance for shoes treatment at all times by performing dehumidification and deodorization on the shoes using a dehumidifying material to refresh the shoes and regenerating the used dehumidifying material.

An object to be achieved by the present invention is to provide a shoes care device which prevents air used for dehumidification and deodorization of shoes from being exposed to a user by an air circulation structure capable of dehumidifying the air inside an inner cabinet where the shoes are placed by using a dehumidifying material and supplying the dehumidified air again to the inner cabinet.

An object to be achieved by the present invention is to provide a shoe care device that is capable of effectively preventing water leakage to an unintended portion from occurring during the process of discharging water condensed inside the shoe care device to the outside.

The technical objects of the present disclosure are not restricted to those set forth herein, and other unmentioned technical objects will be clearly understood by one of ordinary skill in the art to which the present disclosure pertains by referencing the detailed description of the present disclosure given below.

Technical Solution

In order to achieve the above and other objects, a shoes care device according to one aspect of the present invention is configured not only to perform dehumidification and deodorization of shoes using a dehumidifying part but also to regenerate the used dehumidifying part. Specifically, the shoes care device is configured not only to collect moisture and bacteria in air ventilated by the dehumidifying part in a module chamber but also to heat and regenerate the dehumidifying part in the module chamber.

In addition, according to one aspect of the present invention, the shoes care device is configured such that the air used for dehumidifying and deodorizing the shoes has an air circulation structure inside the shoes care device. Specifically, a connection path through which air is circulated is formed between an outlet and a nozzle disposed inside an inner cabinet, respectively.

In addition, the shoe care device according to an aspect of the present disclosure is configured to prevent water from leaking into an unintended portion even when water exceeding a water level that can be accommodated in a discharge tank. Specifically, the shoe care device is configured such that a first water level limit hole connected again to the sump is provided under a first drain inlet hole connected to the sump and allowing water to flow into the drain tank therethrough, and discharges water above the water level that can be accommodated in the drain tank to the sump.

In addition, in the shoe care device according to an aspect of the present disclosure, a sump and a drain tank may be disposed in a machine room below the inner cabinet.

In addition, in the shoe care device according to an aspect of the present disclosure, water may be pumped from the sump installed on the bottom surface of the machine room to the drain tank.

In addition, in the shoe care device according to an aspect of the present disclosure, the drain tank may be exposed outside from a first wall on the front surface of the machine room.

In addition, in the shoe care device according to an aspect of the present disclosure, the drain tank may be detachable from the first wall of the front surface of the machine room.

In addition, in the shoe care device according to an aspect of the present disclosure, an accommodation housing in which the discharge tank is accommodated may be provided from the first wall toward the inside of the machine room.

In addition, in the shoe care device according to an aspect of the present disclosure, a second drain inlet hole and a second water level limit hole may be provided in in the accommodation housing.

In addition, in the shoe care device according to an aspect of the present disclosure, a drain inlet pipe may protrude from the second drain inlet hole, and a water level limit pipe may protrude from the first water level limit hole.

In addition, in the shoe care device according to an aspect of the present disclosure, a connection cover may receive water discharged from the second water level limit hole and deliver the water to the sump.

In addition, in the shoe care device according to an aspect of the present disclosure, a portion of the upper surface of the sump may protrude to be connected to the connection cover.

In addition, the shoe care device according to one aspect of the present disclosure may be installed with a water level sensor configured to detect the water level inside the sump.

In addition, the shoe care device according to an aspect of the present disclosure may include, on the regeneration path, a condenser configured to generate condensed water.

In addition, the shoe care device according to an aspect of the present disclosure may be configured to have a height that is reduced from the condenser to the sump.

In addition, in the shoe care device according to an aspect of the present disclosure, a water supply tank may be exposed outside from the first wall on the front surface of the machine room.

In addition, in the shoe care device according to an aspect of the present disclosure, the water supply tank may be detachable from the first wall of the front surface of the machine room.

The technical objects of the present disclosure are not restricted to those set forth herein, and other unmentioned technical objects will be clearly understood by one of ordinary skill in the art to which the present disclosure pertains by referencing the detailed description of the present disclosure given below.

BRIEF DESCRIPTION OF THE DRAWINGS

FIG. 3 illustrates shoes accommodated in an inner cabinet together.

FIGS. 4*a* to 4*c* illustrate a form where a door is included in the shoes care device, and do not illustrate shoes.

FIG. 8*a* illustrates a state in which the door is included in the shoes care device, and does not illustrate the shoes.

FIG. 9 illustrates a state in which the door is included in the shoes care device.

DETAILED DESCRIPTION

Figure 1A:
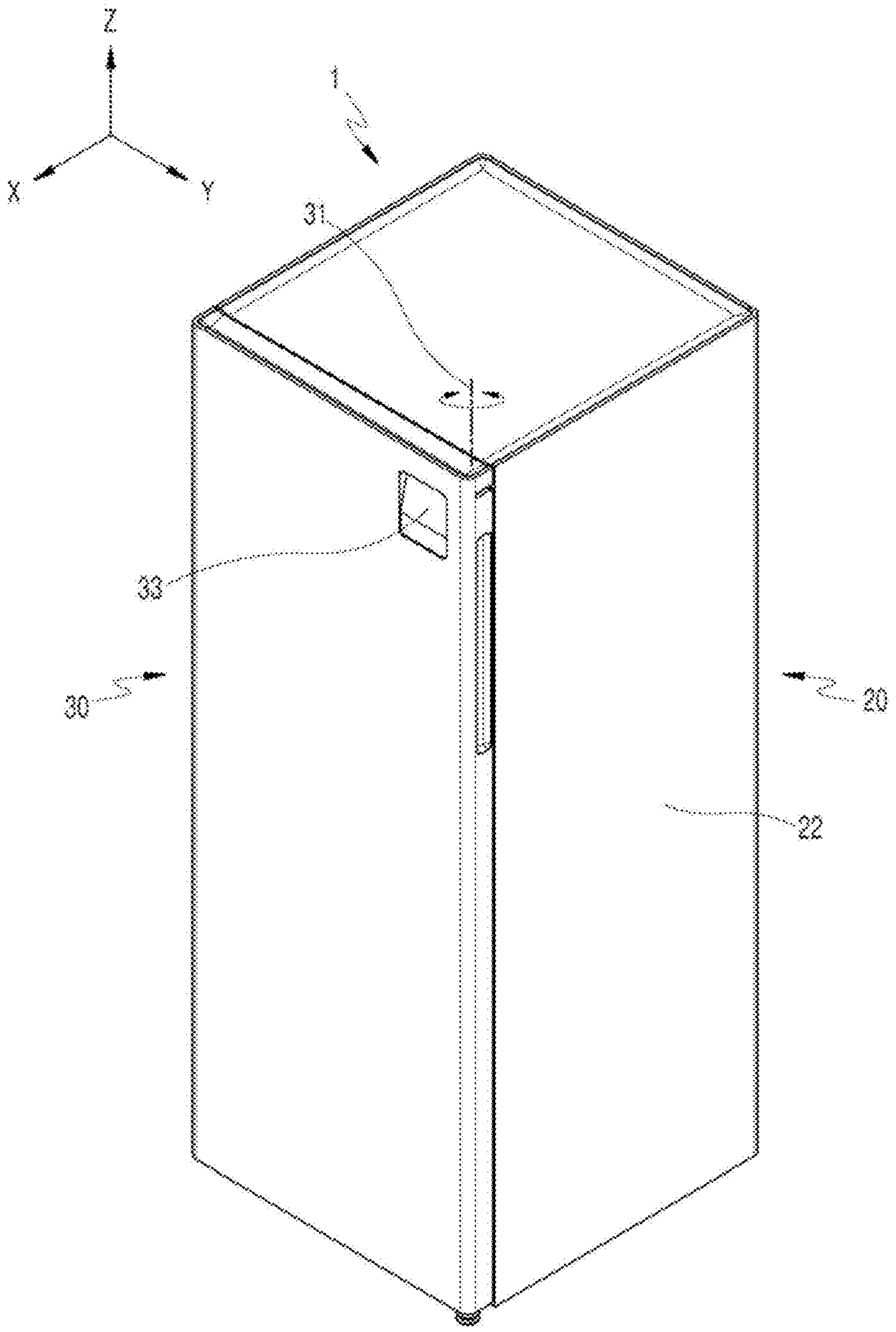
FIG. 1*a* is a perspective view illustrating a shoes care device according to one embodiment of the present invention.

Hereinafter, exemplary embodiments disclosed herein will be described in detail with reference to the accompanying drawings, and like reference numerals designate like elements, and redundant description thereof will be omitted. Suffixes "module" and "unit or portion" for elements used in the following description are merely provided for facilitation of preparing this specification, and thus they are not granted a specific meaning or function. Wherever possible, the same reference numbers will be used throughout the drawings to refer to the same or like parts. In the following description, known functions or structures, which may confuse the substance of the present disclosure, are not explained. The accompanying drawings are used to help easily explain various technical features and it should be understood that the exemplary embodiments presented herein are not limited by the accompanying drawings. As such, the present disclosure should be construed to extend to any alterations, equivalents and substitutes in addition to those which are particularly set out in the accompanying drawings.

Although the terms first, second, and the like, may be used herein to describe various elements, these elements should not be limited by these terms. These terms are generally only used to distinguish one element from another.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present.

The singular expressions include plural expressions unless the context clearly dictates otherwise.

It should be understood that the terms "comprises," "comprising," "includes," "including," "containing," "has," "having" or any other variation thereof specify the presence of stated features, integers, steps, operations, elements, and/or components, but do not preclude the presence or addition of one or more other features, integers, steps, operations, elements, and/or components.

A first direction (X direction), a second direction (Y direction), and a third direction (Z direction) described in one embodiment of the present invention may be directions orthogonal to each other.

Each of the first direction (X direction) and the second direction (Y direction) may be a direction parallel to the horizontal direction, and the third direction (Z direction) may be a direction parallel to the vertical direction. When the first direction (X direction) is parallel to a left-right direction, the second direction (Y direction) may be parallel to a front-rear direction. When the first direction (X direction) is parallel to the front-rear direction, the second direction (Y direction) may be parallel to the left-right direction.

FIG. 1*a* is a perspective view illustrating a shoes care device according to one embodiment of the present invention.

Figure 1B:
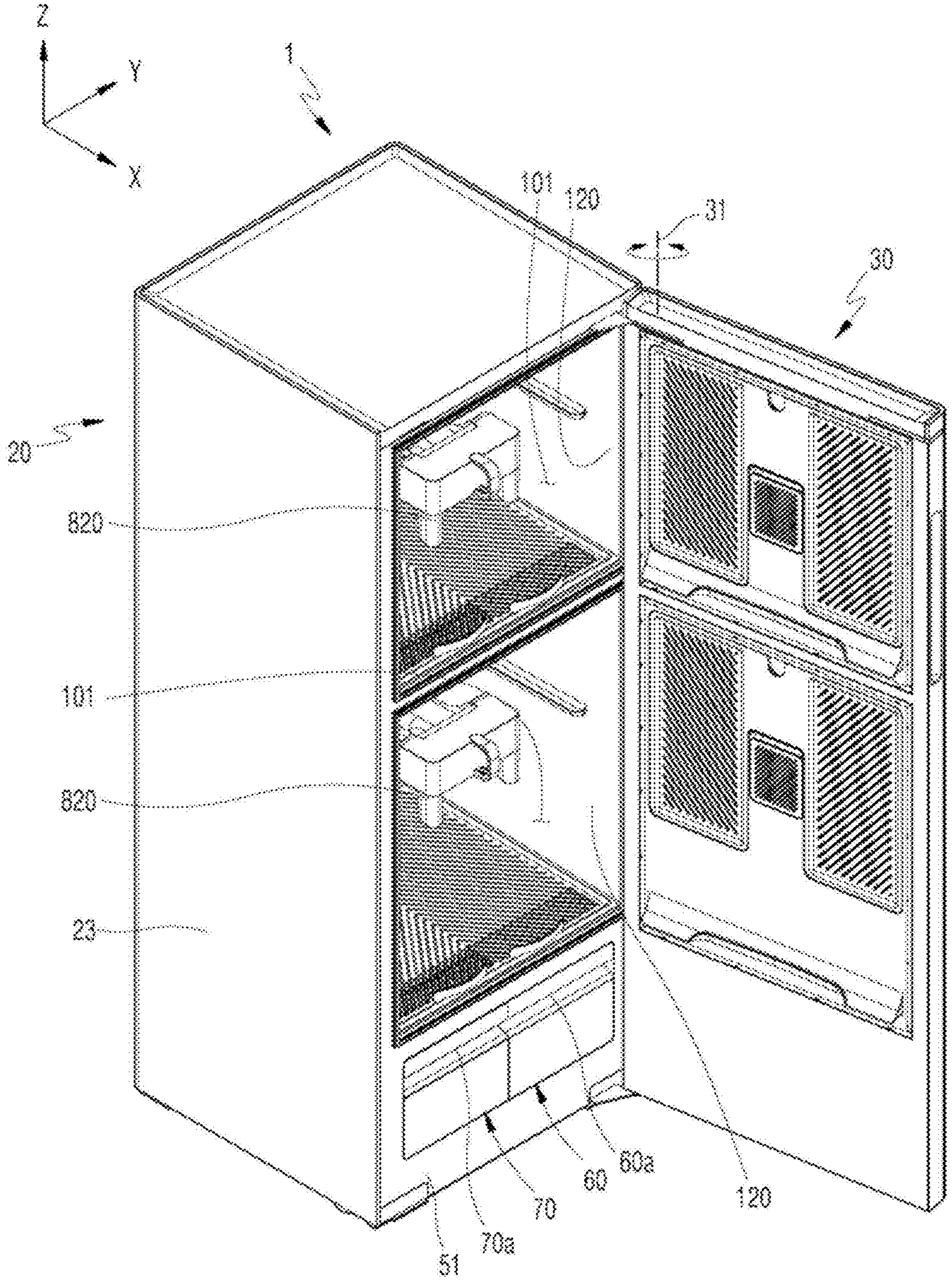
FIG. 1*b* is a perspective view of the shoes care device of FIG. 1*a*, when viewed from another direction, illustrating a state in which a door is opened.

FIG. 1*b* is a perspective view of the shoes care device of FIG. 1*a*, when viewed from another direction, illustrating a state in which a door is opened.

Figure 2A:
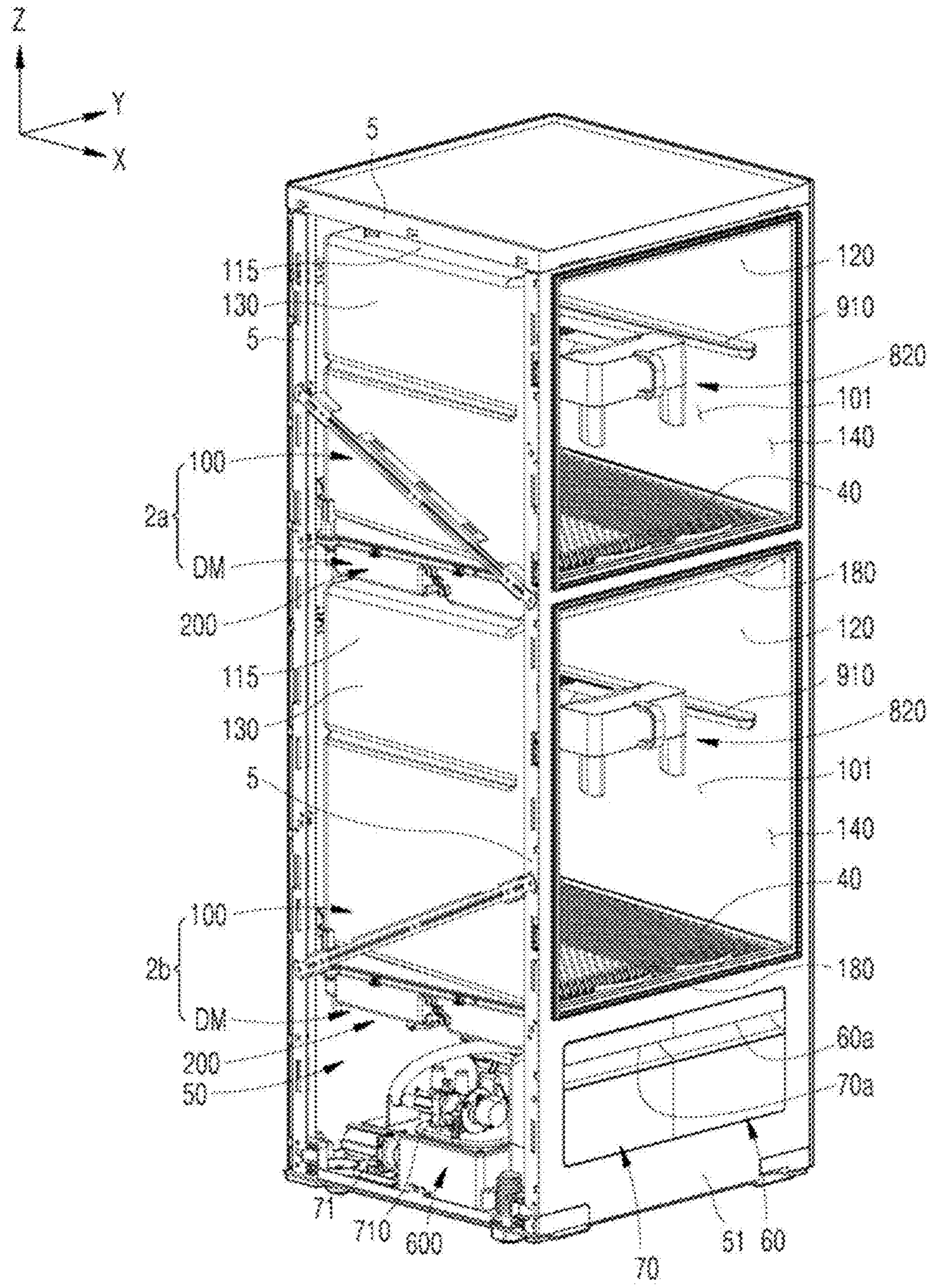
FIG. 2*a* is a perspective view illustrating a state in which a part of the door and an outer cabinet are removed from the shoes care device of FIG. 1*b*.

FIG. 2*a* is a perspective view illustrating a state in which a part of the door and an outer cabinet are removed from the shoes care device of FIG. 1*b*.

Figure 2B:
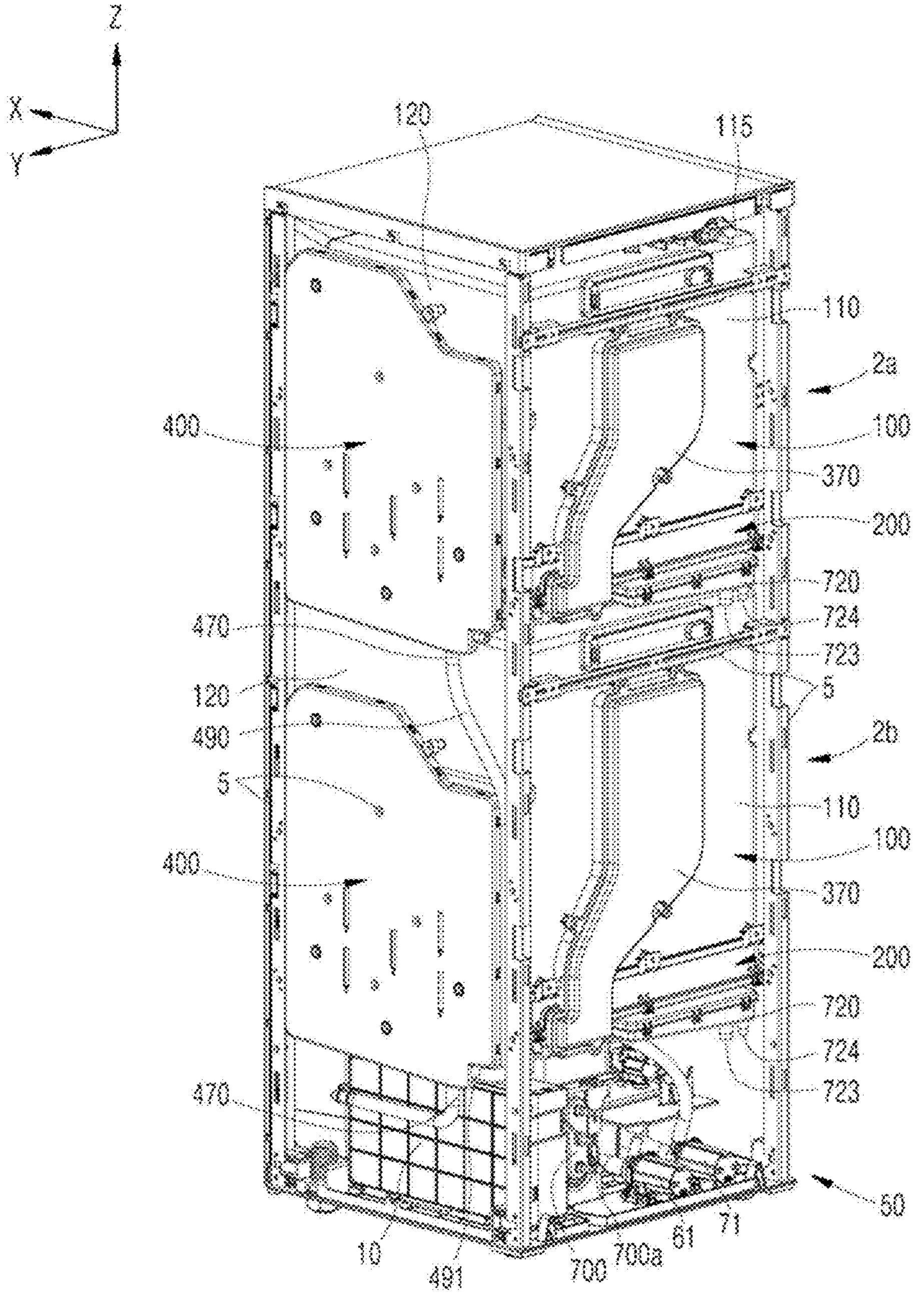
FIG. 2*b* is a perspective view illustrating a state in which the shoes care device illustrated in FIG. 2*a* is viewed from another direction.

FIG. 2*b* is a perspective view illustrating a state in which the shoes care device illustrated in FIG. 2*a* is viewed from another direction.

A shoes care device 1 according to one embodiment of the present invention may include an outer cabinet 20, a door 30, an inner cabinet 100, and a machine room 50. The shoes care device 1 may include a main frame 5.

The outer cabinet 20 and the door 30 may form an overall appearance of the shoes care device 1. The outside of the shoes care device 1 may be formed in a hexahedral shape. That is, while the outer cabinet 20 and the door 30 are coupled to each other and the door 30 is closed, the appearance of the shoes care device 1 may be formed in a hexahedral shape. However, the shoes care device 1 according to one embodiment of the present invention is not limited to such a shape and may have various three-dimensional shapes.

When the door 30 forms the front of the shoes care device 1, the outer cabinet 20 may form an upper side surface, a left-side surface, a right-side surface, a rear surface, and bottom surfaces of the shoes care device 1.

The main frame 5 may form an overall framework of the shoes care device 1. The main frame 5 may have a hexahedral structure.

The outer cabinet 20 may be detachably fixed to the main frame 5.

The outer cabinet 20 may include an outer rear plate 21, a first outer side plate 22, and a second outer side plate 23.

The outer rear plate 21, the first outer side plate 22, and the second outer side plate 23 may be formed integrally with each other, or the outer rear plate 21, the first outer side plate 22, and the second outer side plate 23 may be individually formed.

The outer rear plate 21 forms a vertically erected wall surface. The outer rear plate 21 may form a surface orthogonal to the first direction (X direction). The outer rear plate 21 may form a rear wall surface in the first direction (X direction) on the outer cabinet 20. The outer rear plate 21 may form a rear surface in the first direction (X direction) in the shoes care device 1. The outer rear plate 21 may form an entire outer rear surface of the shoes care device 1.

The first outer side plate 22 and the second outer side plate 23 form vertically erected wall surfaces, respectively, and form opposing wall surfaces facing each other.

The first outer side plate 22 is disposed at any one side with respect to a reference plane RP that is parallel to the first direction (X direction) as a horizontal direction and is a vertical plane. The second outer side plate 23 is disposed on the opposite side of the first outer side plate 22 with respect to the reference plane RP. The first outer side plate 22 may form a left wall surface of the outer cabinet 20, and the second outer side plate 23 may form a right wall surface of the outer cabinet 20.

The outer cabinet 20 may be disposed outside the inner cabinet 100 and the machine room 50 to form an outer wall surface of the machine room 50. When a separate cabinet for the machine room 50 is not provided in the shoes care device 1, the outer cabinet 20 may form a wall separating the machine room 50 from the outside.

The door 30 is configured to open and close the inside of the shoes care device 1. The door 30 may form any one surface of the shoes care device 1. The door 30 may form a left side or a right side of the shoes care device 1, or may form a front side of the shoes care device 1. In the shoes care device 1, the door 30 may be hinge-coupled.

In one embodiment, the door 30 may be hinge-coupled to the main frame 5. In another embodiment, the door 30 may be hinge-coupled to the outer cabinet 20, and in another embodiment, the door 30 may be hinge-coupled to the inner cabinet 100 and/or the machine room 50.

A hinge rotation axis 31 of the door 30 may be formed in the vertical direction. That is, in the shoes care device 1, the door 30 may be configured to be rotatable bidirectionally around a rotation axis 31 in the vertical direction.

In one embodiment, the shoes care device 1 may include one door 30. In another embodiment, the shoes care device 1 may include two or more doors.

When two doors are provided in the shoes care device 1, each door may be individually rotated around each rotation axis.

The first direction (X direction) described in one embodiment of the present invention may be parallel to or substantially parallel to the horizontal direction.

In one embodiment, the first direction (X direction) may be a direction from the rear of the shoes care device 1 to the front.

Hereinafter, except for a particularly limited case, it will be described that the door 30 is formed in a front side of the shoes care device 1. That is, a surface on which the door 30 is formed in the shoes care device 1 is described as a front surface of the shoes care device 1.

Furthermore, hereinafter, except for a particularly limited case, it will be described that the first direction (X direction) is parallel to the front-rear direction, the second direction (Y direction) is parallel to the left-right direction, and the third direction (Z direction) is parallel to the vertical direction.

The inner cabinet 100 and the machine room 50 may be provided inside the outer cabinet 20.

The inner cabinet 100 may be formed in a box shape, and a predetermined space may be formed therein. The space inside the inner cabinet 100 forms an accommodation space 101, and shoes S may be accommodated in the accommodation space 101.

A plurality of shoes S may be disposed together in the accommodation space 101 of one inner cabinet 100.

The inner cabinet 100 may be fixed to the main frame 5.

The inner cabinet 100 has a predetermined size along the first direction (X direction), the second direction (Y direction), and the third direction (Z direction).

The inner cabinet 100 is formed in the shape of a box opened to any one side. The inner cabinet 100 may be formed in a form opened to the front side of the shoes care device 1. The inner cabinet 100 may be configured to include a main opening 140. The main opening 140 may be provided to open the front side of the inner cabinet 100 in the first direction (X direction). The shoes may be disposed inside the inner cabinet 100 or withdrawn from the inner cabinet 100 through the main opening 140.

The main opening 140 of the inner cabinet 100 may be closed or opened by the door 30.

The inner cabinet 100 may include an inner rear plate 110, a first inner side plate 120, a second inner side plate 130, and an inner upper plate 115.

The inner rear plate 110, the first inner side plate 120, the second inner side plate 130, and the inner upper plate 115 may be formed integrally with each other. The inner cabinet 100 may be made of a single material and be formed by injection molding.

The inner rear plate 110 forms a vertically erected wall surface. The inner rear plate 110 may form a surface orthogonal to the first direction (X direction). The inner rear plate 110 may form a rear wall surface of the inner cabinet 100 in the first direction (X direction). The inner rear plate 110 may be formed parallel to the outer rear plate 21.

The first inner side plate 120 and the second inner side plate 130 form vertically erected wall surfaces, respectively, and form opposing wall surfaces facing each other.

The first inner side plate 120 is dispose on either side with respect to the reference plane RP that is parallel to the first direction (X direction) as the horizontal direction and is a vertical surface. The second inner side plate 130 is disposed on the opposite side of the first inner side plate 120 with respect to the reference plane RP. The first inner side plate 120 forms a left wall surface of the inner cabinet 100, and the second inner side plate 130 forms a right wall surface of the inner cabinet 100.

The first inner side plate 120 may be formed parallel to the first outer side plate 22, and the second inner side plate 130 may be formed parallel to the second outer side plate 23.

In one embodiment of the present invention, the inner cabinet 100 may have the form where a lower part thereof is opened. Accordingly, the inner cabinet 100 includes a lower opening formed by opening the lower part thereof. When the inner cabinet 100 is formed in a hexahedral shape on the whole, the lower opening may be formed large to form all or most of a lower surface of the inner cabinet 100.

However, the shoes care device 1 according to one embodiment of the present invention is not used in a state in which an entire lower part of the inner cabinet 100 is opened, but is used in a state in which the inner cabinet 100 and a module housing 200 are coupled to each other so that the lower opening 150 of the inner cabinet 100 is shielded by the module housing 200. That is, the shoes care device 1 is used so that an upper surface of the module housing 200 forms a bottom surface of the accommodation space 101 of the inner cabinet 100. A further explanation thereof will be described below.

A main shelf 40 may be provided in the inside 101 of the inner cabinet 100. The main shelf 40 may be formed such that the shoes S are settled on an upper surface thereof.

The main shelf 40 may be formed in the form of a plate with a predetermined area, or may be formed in the form of a grill where multiple bars are spaced apart from each other.

One main shelf 40 may be provided, or a plurality of main shelves 40 may be provided.

The main shelf 40 may have a substantially flat plate shape and be disposed on a bottom surface of the inner cabinet 100. The main shelf 40 is settled on an upper side of a module cover 202 of the inner cabinet 100. The main shelf 40 may be disposed on the upper side of the module cover 202 of the inner cabinet 100 in a stacked form.

The main shelf 40 is detachable from the inner cabinet 100, and when the main shelf 40 is withdrawn from the inner cabinet 100, the upper surface of the module housing 200 is exposed.

The main shelf 40 may have a rectangular shape when viewed in a plan view. The size of the main shelf 40 may be a size corresponding to the bottom of the accommodation space 101 of the inner cabinet 100. That is, when the main shelf 40 is disposed inside the inner cabinet 100, the main shelf 40 may form all or most of the bottom of the accommodation space 101 of the inner cabinet 100.

In one embodiment, the machine room 50 may be provided in a lower side of the inner cabinet 100. In the machine room 50, some of the components that constitutes the shoes care device 1 may be accommodated, and, in this case, the components that are accommodated in the machine room 50 may be fixed to a main frame 5 or to the inner cabinet 100 or the outer cabinet 20.

Figure 3:
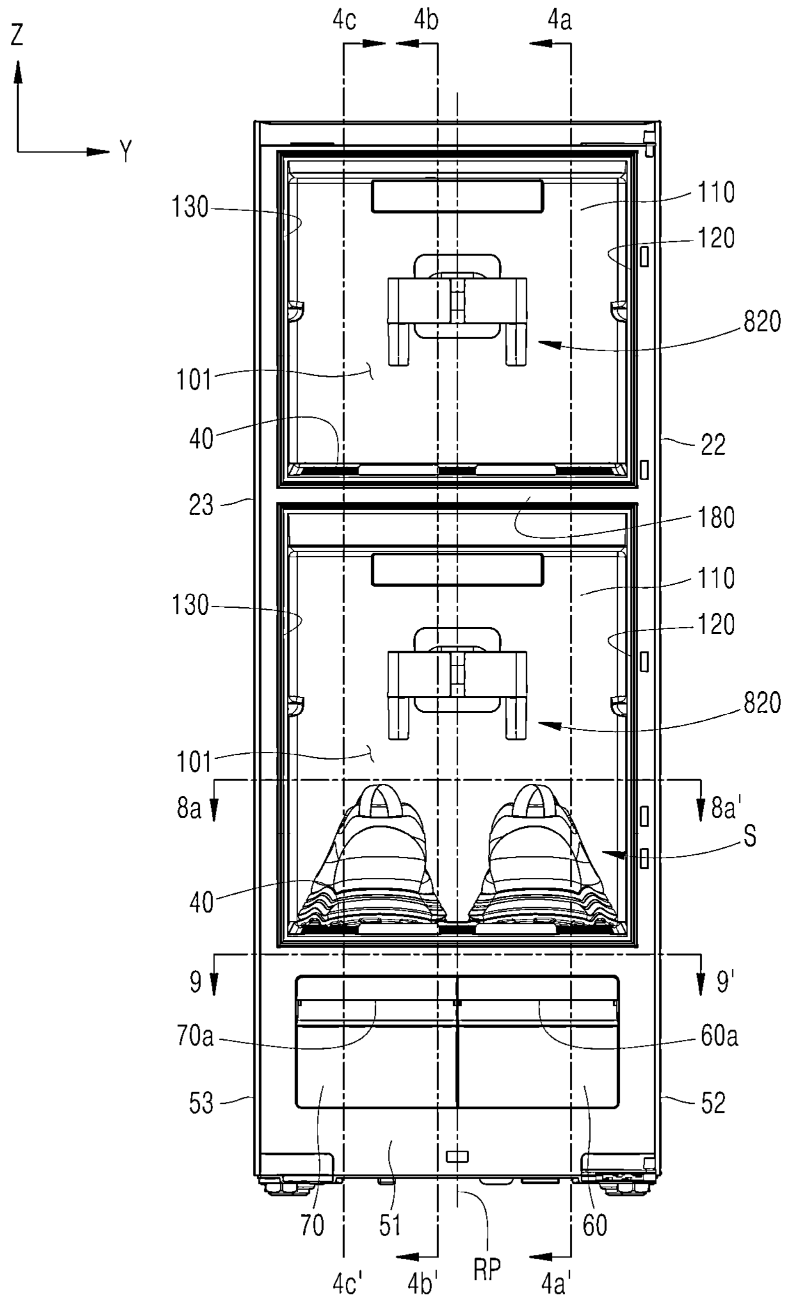
FIG. 3 is a front view illustrating a state in which a door is removed from the shoes care device illustrated in FIG. 1*b*.

FIG. 3 is a front view illustrating a state in which a door is removed from the shoes care device illustrated in FIG. 1*b*. FIG. 3 illustrates shoes accommodated in an inner cabinet together.

Figure 4A:
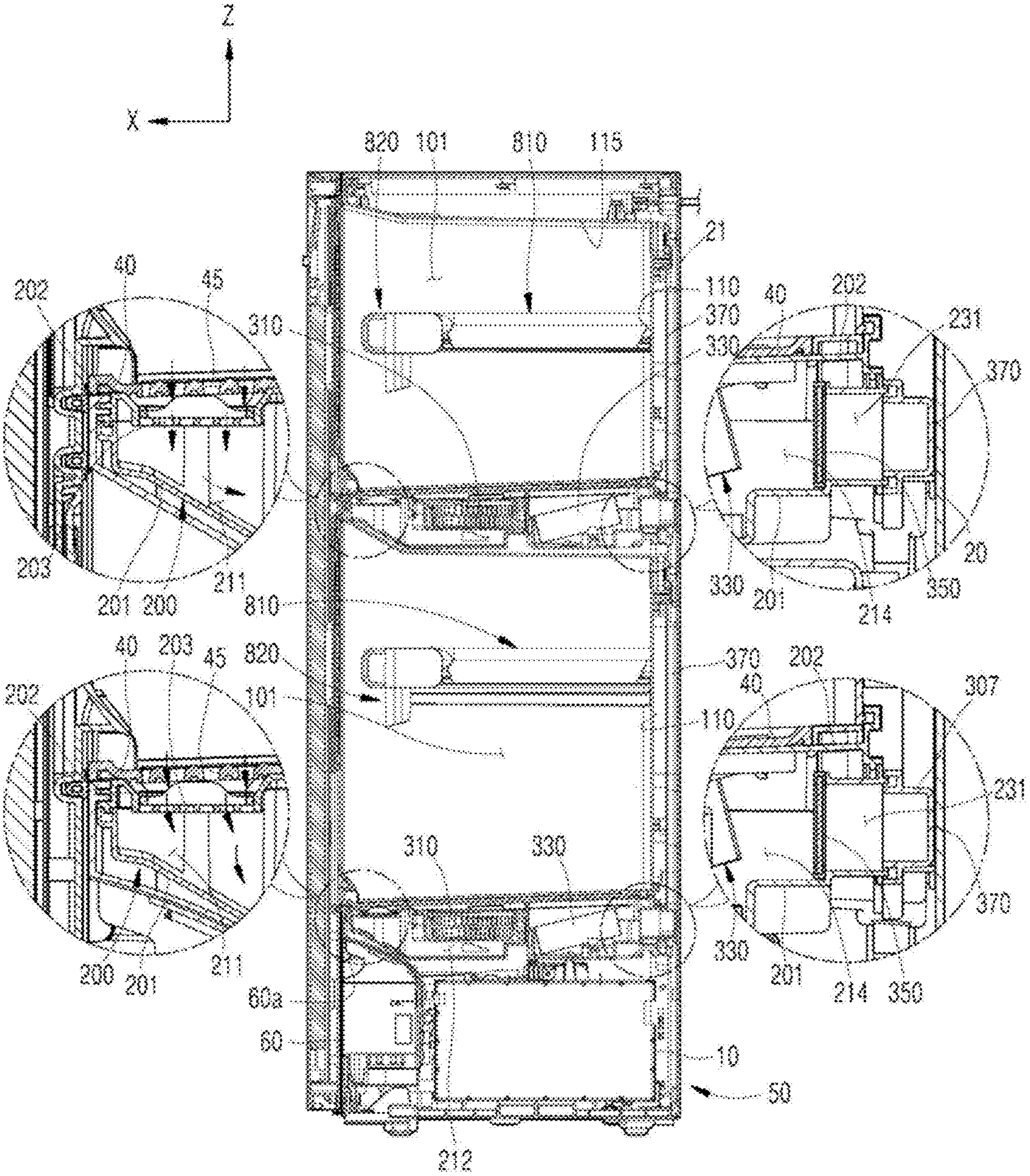
FIG. 4*a* is a cross-sectional view taken along line 4*a*-4*a'* of the shoes care device illustrated in FIG. 3.
Figure 4B:
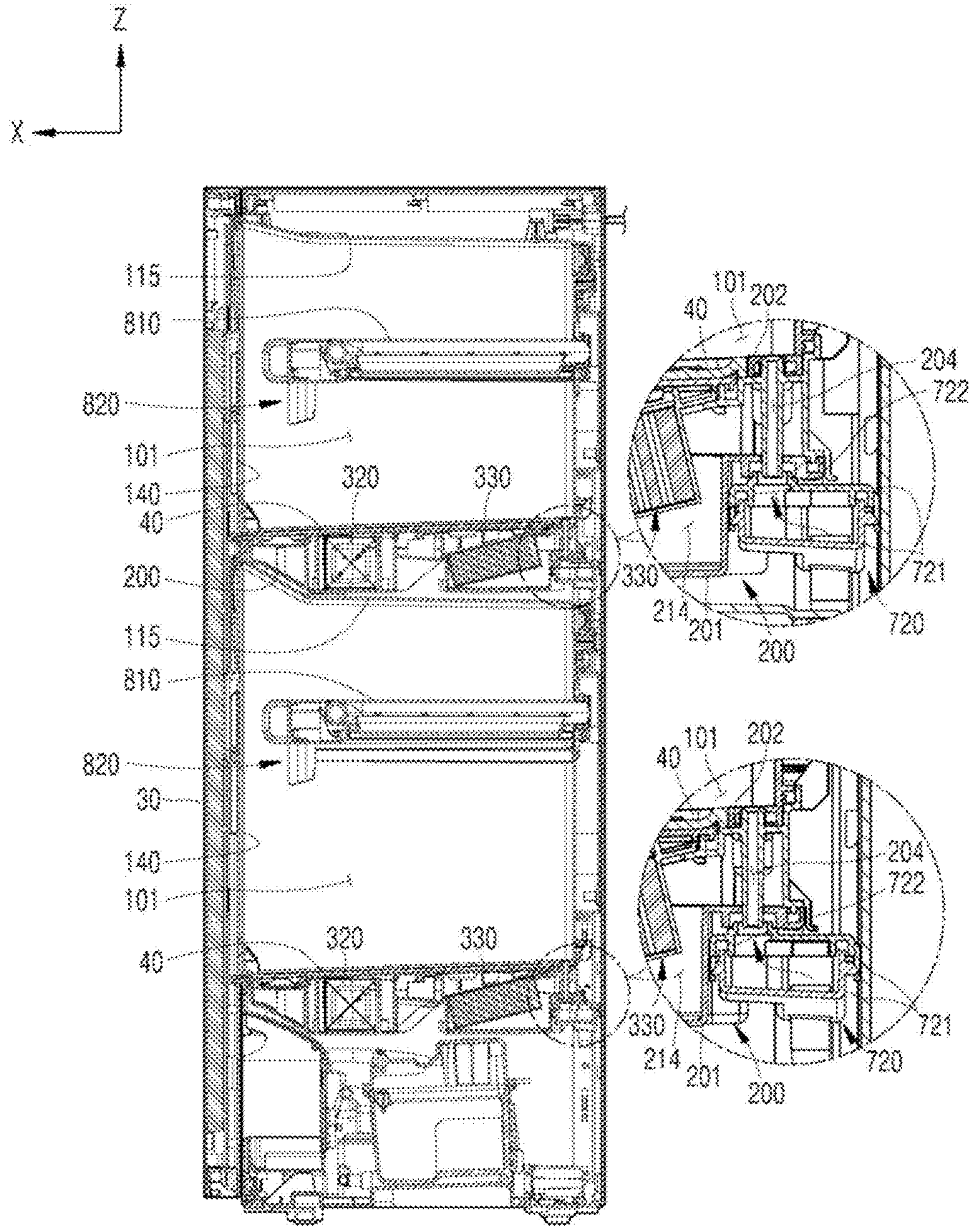
FIG. 4*b* is a cross-sectional view taken along line 4*b*-4*b'* of the shoes care device illustrated in FIG. 3.
Figure 4C:
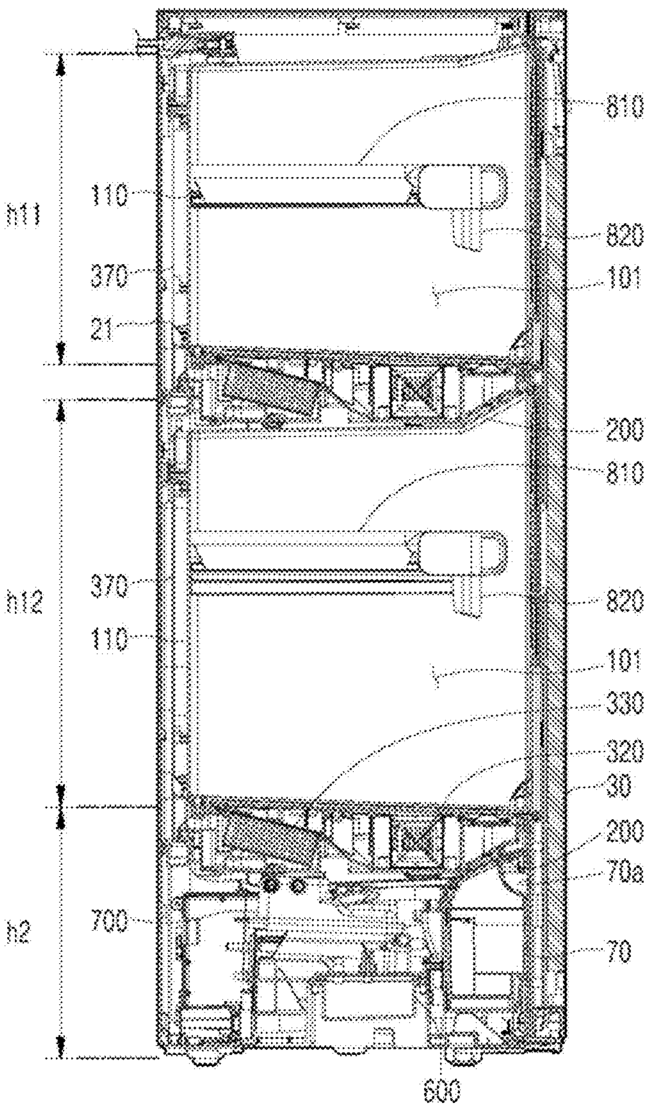
FIG. 4*c* is a cross-sectional view taken along line 4*c*-4*c*' of the shoes care device illustrated in FIG. 3.

FIG. 4*a* is a cross-sectional view taken along line 4*a*-4*a*' of the shoes care device illustrated in FIG. 3, FIG. 4*b* is a cross-sectional view taken along line 4*b*-4*b*' of the shoes care device illustrated in FIG. 3, and FIG. 4*c* is a cross-sectional view taken along line 4*c*-4*c*' of the shoes care device illustrated in FIG. 3. FIGS. 4*a* to 4*c* illustrate a form where a door is included in the shoes care device, and do not illustrate shoes.

The shoes care device 1 according to one embodiment of the present invention includes management devices 2*a* and 2*b*. In the shoes care device 1, a plurality of management devices 2*a* and 2*b* may be provided. In one embodiment, the shoes care device 1 may include a first management device 2*a* and a second management device 2*b*. That is, the shoes care device 1 may include two separate management devices 2*a* and 2*b*.

The 'management device' described in the present invention may refer to a 'first management device 2*a*' and a 'second management device 2*b*', respectively, except for a particularly limited case.

The management devices 2*a* and 2*b* include the above-described inner cabinet 100.

In one embodiment of the present invention, since the inner cabinet 100 of the first management device 2*a* and the inner cabinet 100 of the second management device 2*b* may be distinguished from each other, the inner cabinet 100*a* of the first management device 2*a* may refer to a first inner cabinet 100*a*, and inner cabinet 100*b* of the second management device 2*b* may refer to a second inner cabinet 100*b*.

It may be understood that the 'inner cabinet 100' described in one embodiment of the present invention refers to each of the 'first inner cabinet 100*a*' and the 'second inner cabinet 100*b*', except for a particularly limited case.

When the door 30 is closed in the shoes care device 1, the door 30 closes the main opening 140 of the first management device 2*a* and also closes the main opening 140 of the second management device 2*b*. That is, the door 30 may simultaneously seal the accommodation space 101 of the inner cabinet 100 of the first management device 2*a* and the accommodation space 101 of the inner cabinet 100 of the second management device 2*b*. In this case, the accommodation space 101 of the inner cabinet 100 of the first management device 2*a* and the accommodation space 101 of the inner cabinet 100 of the second management device 2*b* may be configured such that they do not communicate with each other.

As described above, in one embodiment of the present invention, the accommodation space 101 of the inner cabinet 100 of the first management device 2*a* and the accommodation space 101 of the inner cabinet 100 of the second management device 2*b* may form independent spaces, and may form blocked spaces (not communicating with each other). Accordingly, the temperature and humidity of the accommodation space 101 of the first management device 2*a* and the temperature and humidity of the accommodation space 101 of the second management device 2*b* may be controlled differently from each other.

The management devices 2*a* and 2*b* may be configured to include a connection path F10. The management devices 2*a* and 2*b* may be configured to include a blowing part 310 and a dehumidifying part 330. The management devices 2*a* and 2*b* may include an outlet 203 and a nozzle 820.

The management devices 2*a* and 2*b* may include the module housing 200 forming a connection path F10.

The management devices 2*a* and 2*b* may include a regeneration path F20. The management devices 2*a* and 2*b* may include a heating part 320.

The management devices 2*a* and 2*b* may include a conversion flow path F10*a*.

The management devices 2*a* and 2*b* may include a damper 350.

The shoes care device 1 may include a steam generator 700 and a steam valve 710.

The shoes care device 1 may include a sump 600, a water supply tank 60, and a drain tank 70.

Since all or part of the outer cabinet 20 may be spaced apart from the inner cabinet 100, a predetermined gap may be formed between the inner cabinet 100 and the outer cabinet 20.

In a space between the inner cabinet 100 and the outer cabinet 20, components constituting the shoes care device 1 may be provided, and various flow paths constituting the shoes care device 1 may be provided. In one embodiment of the present invention, part of the connection path F10 may be provided between the inner cabinet 100 and the outer cabinet 20, and part of the regeneration path F20 may be provided between the inner cabinet 100 and the outer cabinet 20.

A dry air duct 370 forming the connection path F10 may be provided between the outer rear plate 21 and the inner rear plate 110. Furthermore, a condenser 400 forming the regeneration path F20 may be provided between the first outer side plate 22 and the first inner side plate 120.

The connection path F10 forms a flow path of a fluid.

The connection path F10 forms a passage through which air and/or condensed water inside the shoes care device 1 moves.

The dehumidifying part 330 is disposed inside the connection path F10 and includes a dehumidifying material. The dehumidifying part 330 may be entirely formed of the dehumidifying material, or a part thereof may be formed of the dehumidifying material. A further explanation of the dehumidifying part 330 will be described below.

According to one embodiment of the present invention, the shoes care device 1 has an air circulation structure in which the air inside the inner cabinet 100 in which the shoes are disposed is sucked into the connection path F10 to dehumidify the air using a dehumidifying material 331 and the dehumidified air may be supplied back into the inner cabinet 100.

The connection path F10 may be used as a means to achieve such an air circulation structure in the shoes care device 1. All or part of the connection path F10 may be formed of a pipe, a hose, a tube, a duct, a housing, or a combination thereof.

The module housing 200 according to one embodiment of the present invention forms part of the connection path F10.

The outlet 203 is formed in the module housing 200. The outlet 203 communicates with the accommodation space 101 of the inner cabinet 100, and forms an inlet of the module housing 200 through which the air of the accommodation space 101 of the inner cabinet 100 is suctioned into the module housing 200. The outlet 203 may be disposed below the main shelf 40. In this case, the main shelf 40 may be formed so as not to block the air in the accommodation space 101 from being sucked into the outlet 203. To this end, when the main shelf 40 is formed in a plate shape, a plurality of holes 45 penetrating in the vertical direction may be formed in the main shelf 40 so as to move the air.

In the shoes care device 1, the inner cabinet 100 and the machine room 50 may form a space separated from each other. Furthermore, the module housing 200 that is part of the management devices 2*a* and 2*b* may be provided between the inner cabinet 100 and the machine room 50.

The inner cabinet 100, the module housing 200, and the machine room 50 are provided inside the shoes care device 1 according to one embodiment of the present invention.

The inner cabinet 100, the module housing 200, and the machine room 50 may be continuously arranged from the upper side to the lower side. When the shoes care device 1 according to one embodiment of the present disclosure includes the first management device 2*a* and the second management device 2*b*, the first management device 2*a* may be disposed above the second management device 2*b*. That is, the first management device 2*a*, the second management device 2*b*, and the machine room 50 may be continuously arranged from the upper side to the lower side.

Since the first management device 2*a* and the second management device 2*b* include the inner cabinet 100 and the module housing 200, respectively, they may be continuously arranged in an order of the inner cabinet 100 of the first management device 2*a*, the module housing 200 of the first management device 2*a*, the inner cabinet 100 of the second management device 2*b*, the module housing 200 of the second management device 2*b*, the machine room 50 from the upper side to the lower side.

The inner cabinet 100 may form a space that mainly accommodates an article (shoes S) to be managed, and the module housing 200 and the machine room 50 may form a space that mainly accommodates components for an operation of the shoes care device 1.

In the shoes care device 1 according to one embodiment of the present invention, the blowing part 310, the dehumidifying part 330 (and the dehumidifying material 331), and the heating part 320 may be accommodated inside the module housing 200.

In addition, the machine room 50 may be configured to accommodate a controller 10, the sump 600, the steam generator 700, and the steam valve 710 therein. Furthermore, the machine room 50 may be configured to accommodate the water supply tank 60 and the drain tank 70.

Among the components constituting the management devices 2*a* and 2*b*, components not included in the module housing 200 may be fixedly coupled to the inner cabinet 100 and the outside of the module housing 200 or may be fixedly coupled to the main frame 5.

Components coupled to or accommodated in the machine room 50 may be fixedly coupled to the machine room 50.

The machine room 50 may include a first wall 51.

A first wall 51 forms one wall surface of the machine room 50. The first wall 51 may be erected in the vertical direction, or may be erected in the substantially vertical direction. In one embodiment, the first wall 51 may form a wall surface orthogonal to or inclined with the first direction (X direction).

The first wall 51 may form a front wall surface of the machine room 50, a left wall of the machine room 50, or a right wall of the machine room 50.

The machine room 50 may include a second wall 52 and a third wall 53. The second wall 52 and the third wall 53 form opposite wall surfaces facing each other in the machine room 50. The second wall 52 and the third wall 53 may be erected in the vertical direction, or may be erected in the substantially vertical direction.

When the first wall 51 forms a front wall of the machine room 50, the second wall 52 may form a left wall of the machine room 50, and the third wall 53 may form a right wall of the machine room 50.

The first wall 51 may be formed integrally with the inner cabinet 100, and the second wall 52 and the third wall 53 may be formed integrally with the outer cabinet 20, respectively.

Each of the water supply tank 60 and the drain tank 70 may be formed in the form of a container for accommodating water.

The water supply tank 60 may be configured to store water supplied into the shoes care device 1 inside. The water supply tank 60 may be configured to store water supplied into the steam generator 700 inside.

In order to supply water from the water supply tank 60 into the shoes care device 1, a water pump 61 may be connected to the water supply tank 60. The water supply tank 60 and the first water pump 61 may be connected by a pipe, a hose, etc.

The drain tank 70 may be configured to store water discharged from the shoes care device 1 inside. The drain tank 70 may store water condensed inside the shoes care device 1. The drain tank 70 may be configured to store water drained from the sump 600.

In order to discharge water to the drain tank 70, a water pump 71 (a second water pump) may be connected to the drain tank 70. The drain tank 70 and the second water pump 71 may be connected by a pipe, a hose, etc.

The water supply tank 60 and the drain tank 70 may be coupled to the machine room 50 to get exposed from the outside of one wall surface of the machine room 50.

The water supply tank 60 and the drain tank 70 may be disposed in front of the machine room 50.

The water supply tank 60 and the drain tank 70 may form one wall surface of the machine room 50 along with the first wall 51. When the first wall 51 forms a front surface of the machine room 50, the water supply tank 60 and the drain tank 70 may be exposed from a front side of the machine room 50, and may be coupled to the machine room 50 to get exposed from the outside of the first wall 51.

As the water supply tank 60 and the drain tank 70 are exposed to the outside of the first wall 51, a user may inject water into the water supply tank 60 or discharge water from the drain tank 70.

The water supply tank 60 and the drain tank 70 may be configured to be detachable from the machine room 50. The water supply tank 60 and the drain tank 70 may be detached from the first wall 51. In order to facilitate the attachment and detachment of the water supply tank 60 and the drain tank 70, a handle 60*a* of the water supply tank 60 may be formed on an outer surface of the water supply tank 60, and a handle 70*a* of the drain tank 70 may be formed on an outer surface of the drain tank 70.

Each of the water supply tank 60 and the drain tank 70 may be configured to be separated from the machine room 50 in an outer direction of the first wall 51.

The controller 10 may be configured to control operations of each component in connection with each component constituting the shoes care device 1.

In order to control the controller 10, the shoes care device 1 may be provided with a storage medium in which an application program is stored, and the controller 10 may be configured to control the shoes care device 1 by driving an application program according to information input to the shoes care device 1 and information output from the shoes care device 1.

The controller 10 may control the first management device 2*a* and the second management device 2*b* constituting the shoes care device 1 to operate individually. The controller 10 may control the first management device 2*a* and the second management device 2*b* to operate in different states, and may control shoes (e.g., sneakers) in the first management device 2*a* and shoes (e.g., heels) in the second management device 2*b* to be managed under different conditions. Furthermore, the controller 10 may control the first management device 2*a* and the second management device 2*b* to interwork with each other.

The door 30 may be disposed on either the inner cabinet 100 or the machine room 50 on the same side as the first wall 51. When the door 30 forms the front surface of the shoes care device 1, the first wall 51 forms the front surface of the machine room 50, and the door 30 is disposed directly outside the first wall 51.

In one embodiment of the present invention, the door 30 may be configured to open and close the inner cabinet 100 and further expose or shield the front surface of the machine room 50.

The door 30 may be configured to expose or shield the inner cabinet 100, the water supply tank 60, and the drain tank 70.

As described above, in the shoes care device 1, the door 30, the water supply tank 60, and the drain tank 70 are formed on the same side, and when the door 30 is opened, the water supply tank 60 and the drain tank 70 may be exposed and separated from the shoes care device 1.

In the arrangement explained above, even if left and right sides and a rear side of the shoes care device 1 are blocked by other goods or structures, the door 30 may be opened on a front side of the shoes care device 1, and the water supply tank 60 and the drain tank 70 can be separated from or coupled again to the shoes care device 1.

A control panel 33 for controlling the shoes care device 1 is provided on an outer side of the door 30. The control panel 33 may be formed of a touch screen. A control unit (controller 10) is provided in the inner space of the door 30 to control each component of the shoes care device 1 in connection with the control panel 33. The controller 10 may be provided inside the machine room 50.

As illustrated in FIGS. 1*a* and 1*b*, in one embodiment, the door 30 may be configured to simultaneously expose or shield the inner cabinet 100 and the machine room 50.

In another embodiment, the door 30 may be configured to open and close only the inner cabinet 100. In this case, the machine room 50 may not be shielded by the door 30. Furthermore, in this case, the shoes care device 1 according to one embodiment of the present invention may be further provided with a dedicated door of the machine room 50 to open and close the machine room 50 separately from the door 30.

Figure 5:
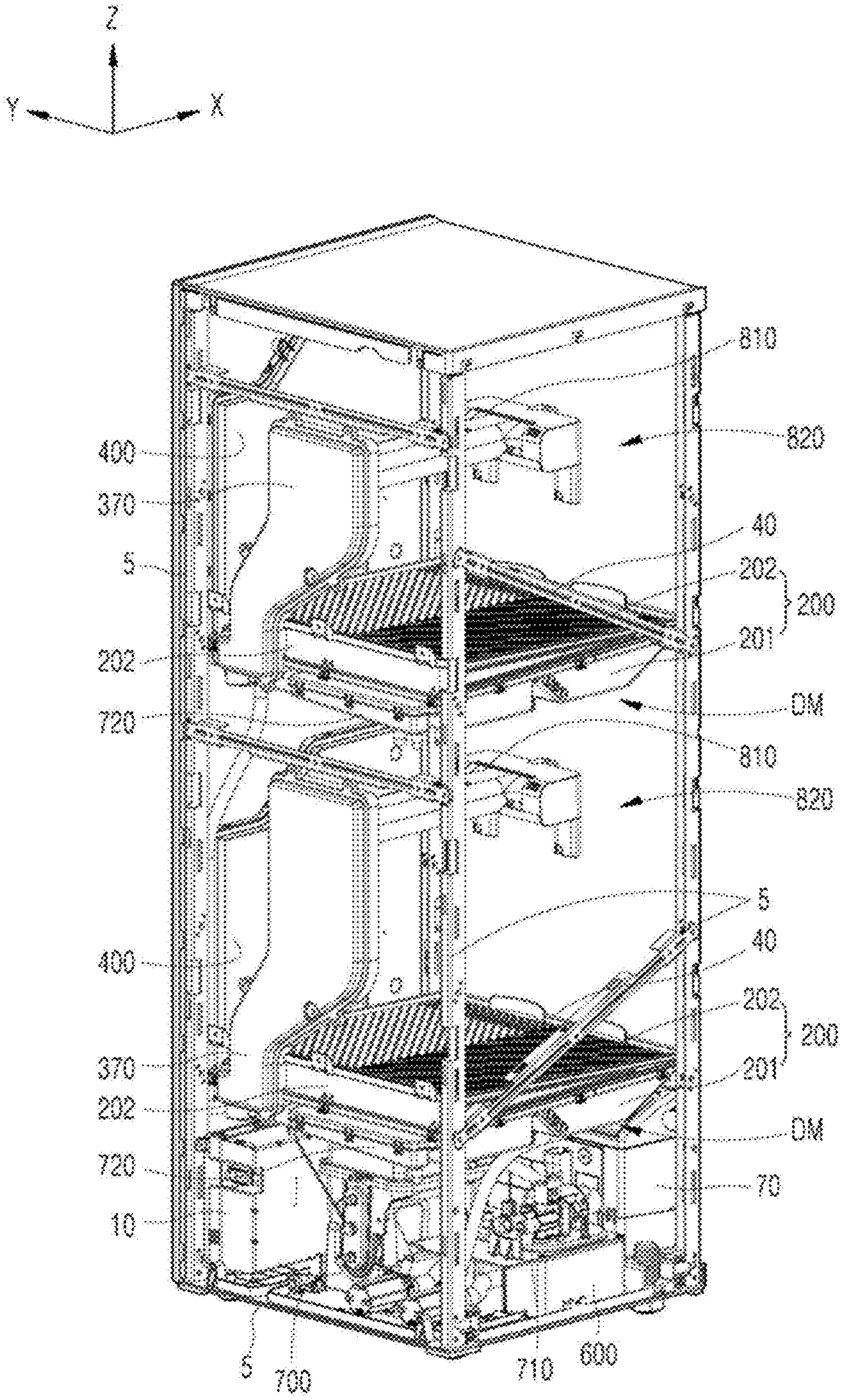
FIG. 5 is a perspective view illustrating a state in which the door, the outer cabinet, and the inner cabinet are removed from the shoes care device according to one embodiment of the present invention.

FIG. 5 is a perspective view illustrating a state in which the door 30, the outer cabinet 20, and the inner cabinet 100 are removed from the shoes care device 1 according to one embodiment of the present invention.

Figure 6:
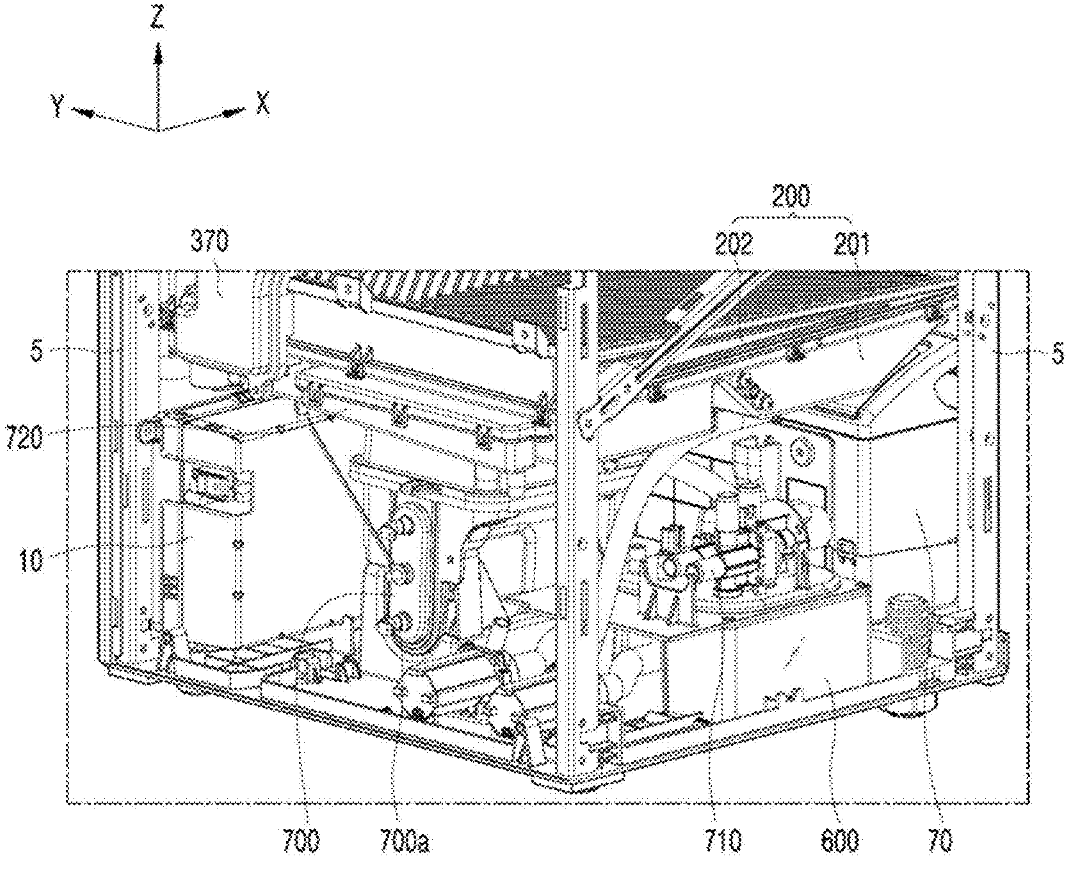
FIG. 6 is a perspective view illustrating a part of a machine room of the shoes care device illustrated in FIG. 5.

FIG. 6 is a perspective view illustrating a machine room part of the shoes care device 1 illustrated in FIG. 5.

Figure 7A:
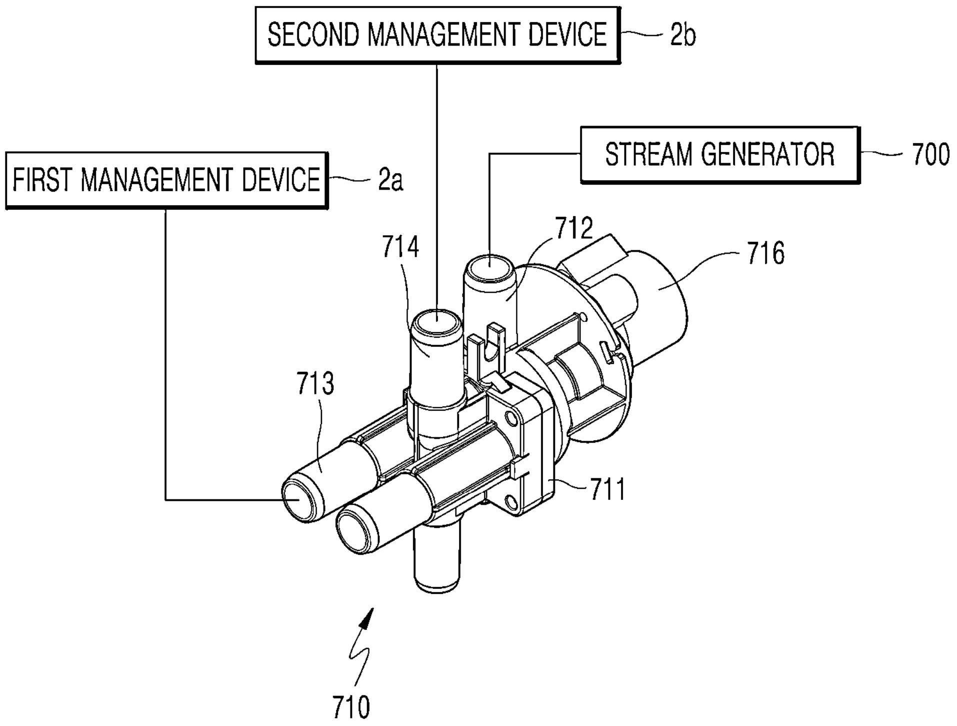
FIG. 7*a* is a view illustrating a steam valve according to one embodiment of the present invention, and illustrating a connection relationship considering the movement of steam.
Figure 7B:
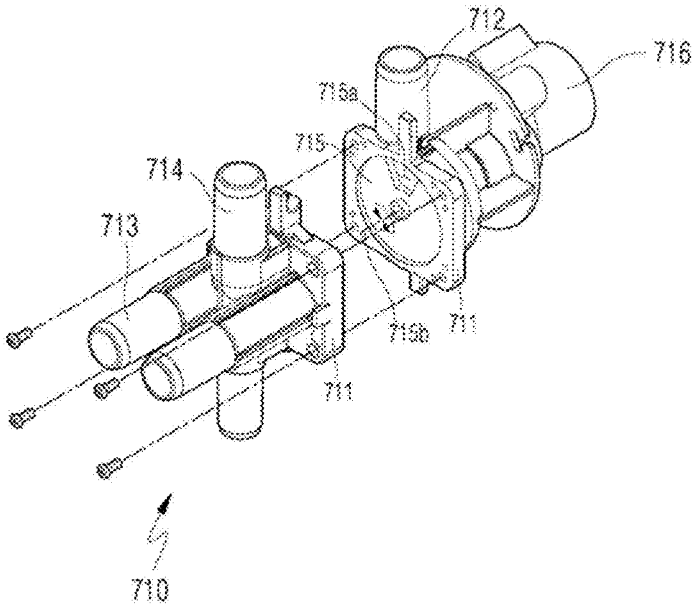
FIG. 7*b* is an exploded perspective view illustrating the steam valve illustrated in FIG. 7*a*.

FIG. 7*a* is a view illustrating the steam valve 710 according to one embodiment of the present invention, and illustrating a connection relationship considering the movement of steam. FIG. 7*b* is an exploded perspective view illustrating the steam valve illustrated in FIG. 7*a*.

The shoes care device 1 is provided with the steam generator 700 as a device configured so as to generate moisture inside the inner cabinet 100. The steam generator 700 may be provided inside the machine room 50. The steam generator 700 is configured to generate steam and selectively supply moisture and steam to the inside of the inner cabinet 100.

The shoes care device 1 according to one embodiment may be provided with one steam generator 700, and the shoes care device 1 according to another embodiment may be provided with two or more steam generators 700.

When the shoes care device 1 is provided with one steam generator 700, the steam generator 700 may be configured to supply steam into the inner cabinet 100 of the first management device 2*a* and/or into the inner cabinet 100 of the second management device 2*b*.

When the shoes care device 1 is provided with two or more steam generators 700, one of the steam generators 700 may supply steam to the inner cabinet 100 of the first management device 2*a*, and the other steam generator 700 may supply steam to the inner cabinet 100 of the second management device 2*b*.

Moist air formed by the steam generator 700 ('air' described in one embodiment of the present invention may be 'air including moisture') is supplied toward the accommodation space 101 of the inner cabinet 100, and moisture may be circulated in the accommodation space 101 of the inner cabinet 100, and accordingly, the moisture may be supplied to the shoes S.

The shoes care device 1 according to one embodiment of the present invention may be a refresher device that refreshes the shoes.

Here, refreshing may refer to a process of removing contaminants, deodorizing, sanitizing, preventing static electricity, or warming by supplying air, heated air, water, mist, steam, etc. to the shoes.

The steam generator 700 may supply steam to the accommodation space 101 of the inner cabinet 100 in which the shoes S are accommodated, and may perform steam treatment on the shoes, which is further meant to exert a refreshing effect due to swelling of shoes materials as well as sterilization by high-temperature steam.

The steam generator 700 is provided with a separate heater 700*a* that heats an inner space and water in the inner space and is configured to heat water to generate steam and supply the heated water to the accommodation space 101 of the inner cabinet 100.

An external faucet, etc., as a water supply source for supplying water to the steam generator 700, may be used, or a container-type water supply tank provided on one side of the machine room 50 may be used. The steam generator 700 may generate steam by receiving water from the water supply tank 60.

The water supply tank 60 and the steam generator 700 may be connected by a pipe, a hose, etc.

The steam generator 700 for the movement of steam and the inner cabinet 100 may be connected by a pipe, a hose, etc. In the shoes care device 1 according to one embodiment of the present invention, as described below, the steam generated by the steam generator 700 may be supplied into the inner cabinet 100 after passing through the steam valve 710 and a steam separator 720. In this case, in order to move the steam, the steam generator 700 and the steam valve 710 may be connected by a pipe, a hose, etc., and the steam valve 710 and the steam separator 720 may also be connected by a pipe, a hose, etc.

The steam valve 710 may be disposed adjacent to the steam generator 700, and the steam valve 710 may be provided in the machine room 50. The steam generator 700 and the steam valve 710 may be provided below the second management device 2*b*.

The steam valve 710 is configured to selectively communicate with each of the accommodation space 101 of the first management device 2*a* and the accommodation space 101 of the second management device 2*b*, respectively.

When the steam of the steam generator 700 is supplied to the accommodation space 101 of the first management device 2*a* and/or the accommodation space 101 of the second management device 2*b*, the steam valve 710 operates to control whether the stream is supplied or not, and an operation of the stream 710 is driven by the controller 10.

The steam valve 710 includes a valve housing 711, a valve inlet 712, a first valve outlet 713, a second valve outlet 714, a valve disk 715, and a valve motor 716. In the steam valve 710 illustrated in FIGS. 7*a* and 7*b*, the other outlets except the valve inlet 712, the first valve outlet 713, and the second valve outlet 714 may be blocked by a stopper and deactivated.

The valve housing 711 forms a body of the steam valve 710, and has a predetermined inner space formed inside.

The valve inlet 712 may have a tubular shape and be coupled to the valve housing 711 to communicate with the inner space of the valve housing 711. The valve inlet 712 is a part connected to the steam generator 700, and steam may flow into the steam valve 710 (inside the valve housing 711) through the valve inlet 712.

The first valve outlet 713 and the second valve outlet 714 may be formed in a tubular shape and be coupled to the valve housing 711 to communicate with the inner space of the valve housing 711.

The first valve outlet 713 and the second valve outlet 714 are outlets through which steam is discharged from the steam valve 710. The first valve outlet 713 is connected to the accommodation space 101 of the first management device 2*a*, and the second valve outlet 714 is connected to the accommodation space 101 of the second management device 2*b*.

The valve disk 715 is provided inside the steam valve 710 (inside the valve housing 711) and is configured to open and close a flow path inside the steam valve 710. The valve disk 715 may be configured to selectively open and close a flow path of the first valve outlet 713 and a flow path of the second valve outlet 714.

The valve disk 715 is disposed between the valve inlet 712 and the first valve outlet 713, or between the valve inlet 712 and the second valve outlet 714, inside the valve housing 711. The valve disk 715 allows the valve inlet 712 and the first valve outlet 713 to communicate with each other or block the communication therewith, and also allows the valve inlet 712 and the second valve outlet 714 to communicate with each other or block the communication therewith.

In one embodiment of the present invention, the valve disk 715 may be formed in a circular plate shape and may include a valve hole 715*a*. The valve hole 715*a* is a hole penetrating the valve disk 715. The valve disk 715 may be rotatably coupled to the valve housing 711 around a valve rotation axis 715*b*, and the valve hole 715*a* may be formed eccentrically from the valve rotation axis 715*b*.

The valve motor 716 is coupled to the valve housing 711, and the valve motor 716 is coupled to the rotation axis 715*b* of the valve disk 715 to rotate the valve disk 715.

The controller 10 may control the steam valve 710 by controlling an operation of the valve motor 716.

The valve disk 715 rotates by the operation of the valve motor 716, and the valve disk 715 opens or closes a flow path inside the steam valve 710 (inside the valve housing 711) depending on the degree of rotation of the valve disk 715.

In one embodiment, depending on the degree of rotation of the valve disk 715, when the valve inlet 712 and the first valve outlet 713 communicate with each other through the valve hole 715*a*, the valve inlet 712 and the second valve outlet 714 are blocked from communicating with each other by the valve disk 715, or when the valve inlet 712 and the second valve outlet 714 communicate with each other through the valve hole 715*a*, the valve outlet 712 and the first valve outlet 713 may be blocked from communicating with each other by the valve disk 715.

In another embodiment, depending on the degree of rotation of the valve disk 715, the valve inlet 712 may communicate with both the first valve outlet 713 and the second valve outlet 714, or the valve inlet 712 may be blocked from communicating with both the first valve outlet 713 and the second valve outlet 714.

In the shoes care device 1 according to one embodiment of the present invention, the valve disk 715 may close a flow path of the second valve outlet 714 while opening a flow path of the first valve outlet 713, and may also close the flow path of the first valve outlet 713 and open the flow path of the second valve outlet 714.

The steam valve 710 made as described above may operate such that only the valve inlet 712 and the first valve outlet 713 communicate with each other, or only the valve inlet 712 and the second valve outlet 714 communicate with each other.

In the arrangement explained above, all the steam generated by the steam generator 700 may be supplied to the accommodation space 101 of the first management device 2*a*, or may be supplied to the accommodation space 101 of the second management device 2*b*. In this case, the steam generated by the steam generator 700 may be supplied to the accommodation space 101 of the first management device 2*a* or the accommodation space 101 of the second management device 2*b* without a pressure drop, and even when only one steam generator 700 is provided in the shoes care device 1, the steam may be sufficiently and stably supplied to the accommodation spaces 101 of each of the two inner cabinets 100.

In one embodiment of the present invention, the controller 10 may control the stream valve 710 such that when the heating part 320 of the first management device 2*a* is turned off (when a heater 321 of the heating part 320 is turned off), the valve disk 715 closes or opens the first valve outlet 713, and when the heating part 320 of the first management device 2*a* is turned on (when the heater 321 of the heating part 320 is turned on), the valve disk 715 closes the first valve outlet 713.

In addition, the controller 10 may control the stream valve 710 such that when the heating part 320 of the second management device 2*b* is turned off (when the heater 321 of the heating part 320 is turned off), the valve disk 715 closes or opens the second valve outlet 714, and when the heating part 320 of the second management device 2*b* is turned on (when the heater 321 of the heating part 320 is turned on), the valve disk 715 closes the second valve outlet 714.

In the shoes care device 1 according to one embodiment of the present invention, by controlling the steam valve 710 by the controller 10, the steam generated in the steam generator 700 may be selectively or simultaneously supplied to the accommodation space 101 of the first management device 2*a* and the accommodation space 101 of the second management device 2*b*, and whether the steam is supplied or not may be controlled according to a use state of the shoes care device 1.

Figure 8A:
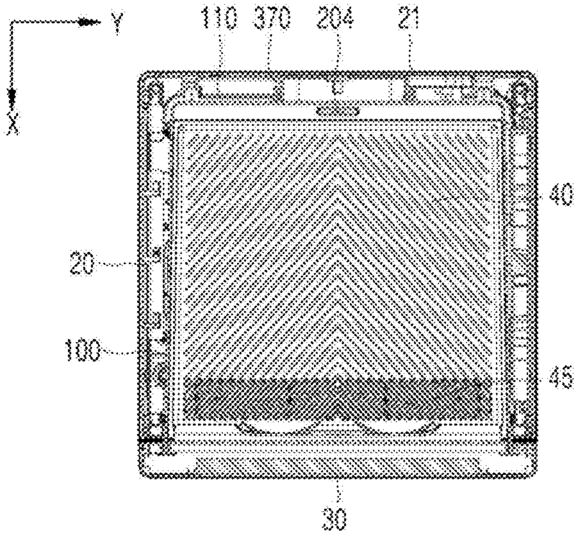
FIG. 8*a* is a cross-sectional view taken along line D-D' of the shoes care device illustrated in FIG. 3.

FIG. 8*a* is a cross-sectional view taken along line 8*a*-8*a*' of the shoes care device 1 illustrated in FIG. 3.

Figure 8B:
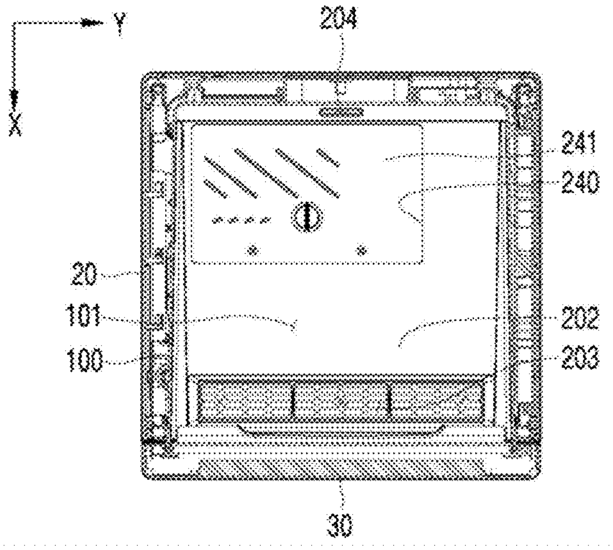
FIG. 8*b* is a view illustrating a state in which a main shelf is removed from the shoes care device illustrated in FIG. 8*a*.

FIG. 8*b* is a view illustrating a state in which the main shelf 40 is removed from the shoes care device 1 illustrated in FIG. 8*a*.

Figure 9:
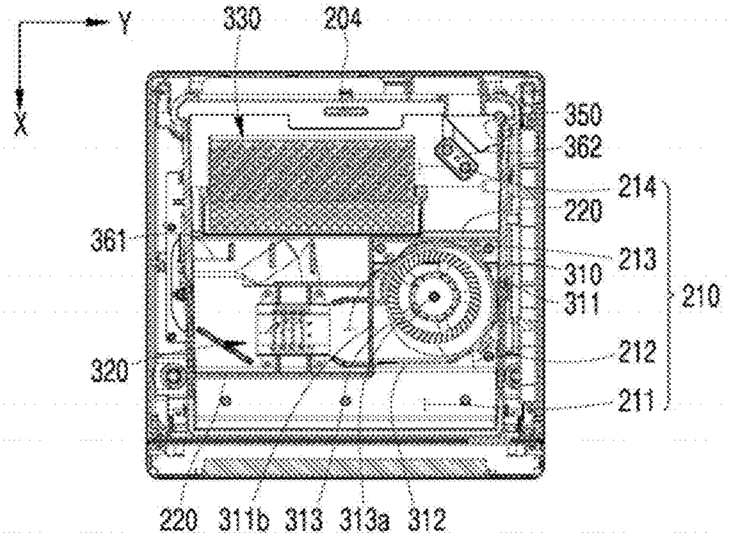
FIG. 9 is a cross-sectional view taken along line E-E' of the shoes care device illustrated in FIG. 3.

FIG. 9 is a cross-sectional view taken along line 9-9' of the shoes care device 1 illustrated in FIG. 3.

Figure 10A:
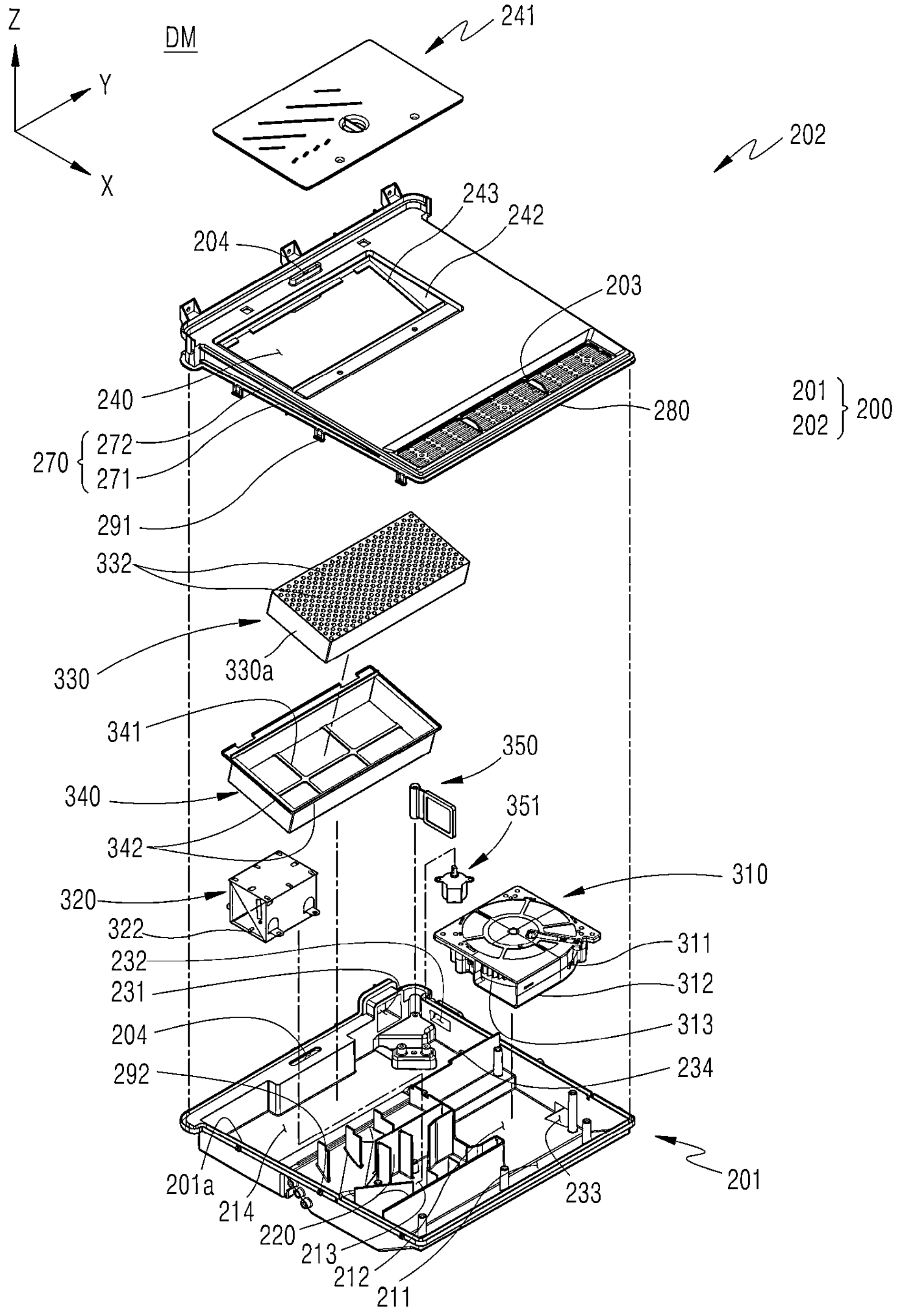
FIG. 10*a* is an exploded perspective view illustrating a drying module in the shoes care device according to one embodiment of the present invention.
Figure 10B:
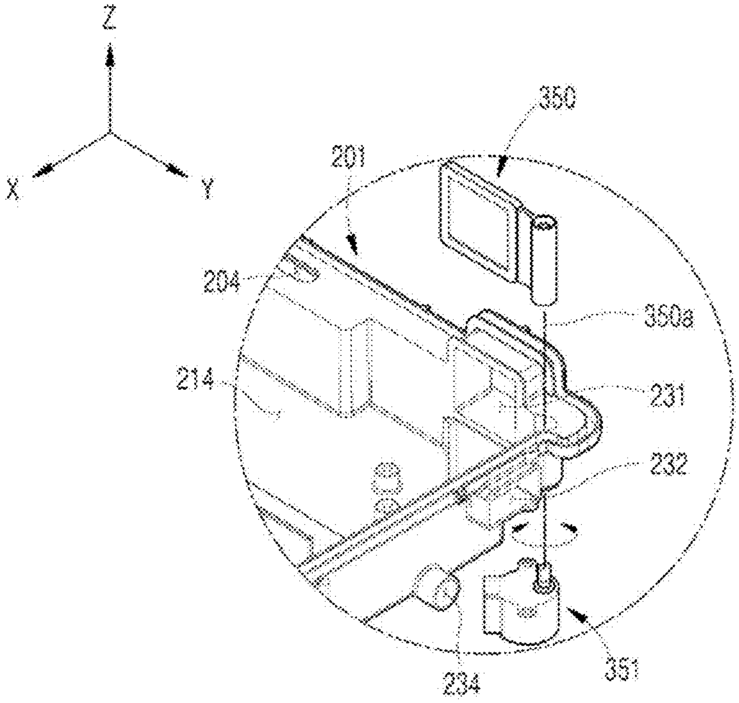
FIG. 10*b* is an exploded perspective view illustrating a partial configuration of the drying module at a part to which a damper is coupled.

FIG. 10*a* is an exploded perspective view illustrating a drying module in the shoes care device 1 according to one embodiment of the present invention. FIG. 10*b* is an exploded perspective view illustrating a partial configuration of the drying module at a part to which the damper 350 is coupled.

In the shoes care device 1 according to one embodiment of the present invention, the dehumidifying part 330 may be used as a means that dehumidifies air.

As described above, the dehumidifying part 330 may be provided inside the module housing 200.

The dehumidifying part 330 is configured to have a predetermined volume. The dehumidifying part 330 may be configured to be porous by itself. A plurality of pores may be formed over an entire volume of the dehumidifying part 330, and air may move by penetrating the dehumidifying part 330 through such pores.

When the dehumidifying part 330 is composed of a combination of a plurality of dehumidifying materials, the plurality of dehumidifying materials may be fixed to each other by a separate fixing means, or may be fixed to each other by adhesion.

The dehumidifying part 330 may be formed of dehumidifying materials, and may be configured to include the dehumidifying materials.

The dehumidifying material 331 according to one embodiment of the present invention is configured to include a material capable of reducing humidity by absorbing moisture in the air. The dehumidifying material 331 may be formed of various materials or a combination of the materials within the range of absorbing or adhering the moisture in the air, and may be formed in various shapes and structures.

The dehumidifying material 331 according to one embodiment of the present invention may be referred to as a desiccant or an adsorbent.

The dehumidifying material 331 according to one embodiment of the present invention may be formed of a microporous material. The dehumidifying material 331 according to one embodiment of the present invention may include silica gel, activated carbon, activated alumina (AL2O3), diatomaceous earth, etc.

Specifically, the dehumidifying material 331 according to one embodiment of the present invention may be formed of zeolite or may be configured to include zeolite.

The zeolite is a natural and synthetic silicate mineral in which tunnels or open channels having a size of approximately 3 to 10 angstroms (Å) are regularly arranged, and may function as dehumidification by adsorbing the moisture in the air.

When the zeolite is heated, moisture adsorbed on the zeolite may be separated into a large amount of steam. According to the characteristics of the zeolite, the zeolite may be regenerated in a state capable of not only performing the dehumidification function to remove the moisture from the air but also performing the dehumidification function by heating the zeolite and separating the moisture adsorbed to the zeolite.

The zeolite may be formed in the form of small grains (or stones) having the size (diameter) of several micrometers to several tens of micrometers, and the dehumidifying material 331 described in one embodiment of the present invention may refer to a combination of the grains (or stones). Each of the grains (or stones) may be agglomerated or combined with each other to form a single structure.

In another embodiment, the dehumidifying part 330 may include a dehumidifying body 330*a* and the dehumidifying material 331.

The dehumidifying body 330*a* may be formed to have a predetermined volume. In one embodiment, the dehumidifying body 330*a* may be formed in a substantially hexahedral shape.

In order to allow air to move through the dehumidifying body 330*a*, the dehumidifying body 330*a* may be provided with a plurality of dehumidification through holes 332 penetrated in one direction. A cross section of the dehumidifying through hole 332 may be formed in a circular shape, a polygonal shape, etc. The dehumidifying through hole 332 may have a hexagonal cross section.

In the dehumidifying body 330*a*, the dehumidifying through hole 332 may all have the same shape and size, or may have different shapes and sizes.

The dehumidifying body 330*a* may be formed of or include materials such as synthetic resin, metal, ceramic, etc. The dehumidifying body 330*a* may be formed of a combination of fibers, and may be formed of a nonwoven fabric, etc.

The dehumidifying material 331 may be coated on the dehumidifying body 330*a*. The dehumidifying material 331 may be coated on the outside and inside of the dehumidifying body 330*a*. Specifically, the dehumidifying material 331 may be coated on a surface in which the dehumidifying through hole 332 is formed.

When the dehumidifying body 330*a* is formed of a combination of fibers, the zeolite may be first coated on each fiber as the dehumidifying material 331, and the zeolite-coated fiber may be processed to form the dehumidifying body 330*a* and simultaneously form the dehumidifying part 330.

Regarding the coating of the zeolite, a manufacturing method of a zeolite coated ceramic paper (Korean Patent No. 10-1004826) is known, and Korean Patent No. 10-1173213 and Korean Patent No. 10-0941521 also describes a method of coating zeolite on a surface of a material. The dehumidifying part 330 according to one embodiment of the present invention may be formed by coating the gelled zeolite precursor on the dehumidifying body 330*a* or materials constituting the dehumidifying body 330*a* and then performing heat treatment when the dehumidifying material 331 is formed of the zeolite.

In one embodiment of the present invention, the coating of the dehumidifying material 331 (zeolite) may be performed by using various known or possible methods, and is not limited to a certain manufacturing method related to the coating of the dehumidifying material 331.

The blowing part 310 is provided inside the connection path F10. A blowing fan 313 may be provided inside the blowing part 310. Since the blowing part 310 is provided in the connection path F10, air flows in the connection path F10 when the blowing part 310 is driven, and since the connection path F10 also communicates with the accommodation space 101 of the inner cabinet 100, the air flows and moves in the accommodation space 101 by driving the blowing part 310.

In this way, the air may be sucked from the inner cabinet 100 into the connection path F10 by the driving of the blowing part 310 (a rotation of the blowing fan 313), and the air inside the connection path F10 may be ventilated.

In one embodiment, the blowing part 310 is provided inside the module housing 200 forming the connection path F10, and the blowing part 310 is driven to suction the air inside the inner cabinet 100 into an inlet 203. The air inside the connection path F10 passes through the module housing 200 constituting the connection path F10, the dry air duct 370, and a nozzle duct 810 and is then discharged back into the inner cabinet 820.

As such, the flow of air may be generated in the shoes care device 1 by the driving of the blowing part 310.

Dry air may be supplied to the inside of the inner cabinet 100 by the blowing part 310.

The heating part 320 is provided at one side of the dehumidifying part 330 and the blowing part 310 in the connection path F10. The heating part 320 may be provided inside the module housing 200. Based on a movement direction of the air inside the module housing 200, the module housing 200 may be arranged in an order of the blowing part 310, the heating part 320, and the dehumidifying part 330. That is, the air introduced into the outlet 203 of the module housing 200 moves along the connection path F10 by passing sequentially through the blowing part 310, the heating part 320, and the dehumidifying part 330.

The heating part 320 is disposed inside the module housing 200 and is configured to heat the air of the module chamber 210 inside the module housing 200.

The heating part 320 may be configured to heat the dehumidifying part 330. The heating part 320 may be configured to heat the dehumidifying material 331 constituting the dehumidifying part 330.

The air heated by the heating part 320 by the driving of the blowing part 310 moves directly to the dehumidifying part 330, thus heating the dehumidifying part 330. To this end, the heating part 320 is disposed inside the module housing 200 adjacent to the dehumidifying part 330. Specifically, the heating part 320 is disposed inside the module housing 200 adjacent to the dehumidifying part 330 based on a movement path of the air inside the module housing 200.

In the module housing 200, the dehumidification by the dehumidifying material 331 or the regeneration of the dehumidifying material 331 may be achieved by selectively heating the heating part 320.

The heating part 320 may be fixedly coupled to the module housing 200 in the module housing 200.

The heating part 320 may be made up of various devices and structures within a range capable of heating the air inside the module housing 200 or supplying heat to the dehumidifying part 330.

The heating part 320 may be formed of an electric heater 321. In one embodiment of the present invention, the heating part 320 may include the heater 321. The heater 321 includes a heating element, and may be configured to supply heat to the periphery while the heating element generates heat by supplied electric energy. The heater 321 may include a nichrome wire as the heating element.

The heater 321 of the heating part 320 may be formed in a ring shape, and the air may move by penetrating the center and surroundings of the ring-shaped heater 321 and be simultaneously heated. The heater 321 of the heating part 320 may be repeatedly formed in a second module chamber 213 along the movement direction of air.

The heater 321 of the heating part 320 may be formed in a circular ring shape or a rectangular ring shape.

The heating part 320 may include a heater flange 322 to which the heater 321 is fixed.

The heater flange 322 may be formed in the form of a metallic plate.

The heater flange 322 may be formed of a combination of flat plates in the second module chamber 213 along the movement direction of air. The heater flange 322 has a cross section that may be formed of a plate shape or a combination of plates in the second module chamber 213 along the movement direction of air (the second direction (Y direction)).

The heater flange 322 may include an outer flange 322*a* and an inner flange 322*b*.

The outer flange 322*a* may be formed in a tubular shape along the second direction (Y direction). An interior of the outer flange 322*a* is provided with a space to move air along the movement direction of air (a direction parallel to the second direction (Y direction)) in the second module chamber 213.

The inner flange 322*b* is fixed to the interior of the outer flange 322*a*. The inner flange 322*b* may include two or more plates crossing each other, and the heater 321 of the heating part 320 may be fixed to the inner flange 322*b*.

The heater flange 322 may be formed in various forms that fix the heater 321 of the heating part 320 and do not interfere with a flow of air moving through the second module chamber 213.

In one embodiment of the present invention, the blowing part 310, the heating part 320, the dehumidifying part 330, and the module housing 200 may form one set.

The set may be provided in a plural form. The shoes care device 1 according to one embodiment may be provided with two sets.

Such a set may be provided in each of the first management device 2*a* and the second management device 2*b*.

Such a set may form a drying module DM in the shoes care device 1 according to one embodiment of the present invention.

That is, in one embodiment of the present invention, the drying module DM may include the module housing 200, the blowing part 310, the heating part 320, and the dehumidifying part 330. Furthermore, the drying module DM is provided in each of the first management device 2*a* and the second management device 2*b*.

In the shoes care device 1 according to one embodiment of the present invention, a plurality of drying modules DM may be provided.

In the shoes care device 1 according to one embodiment of the present invention, a pair of drying modules DM may be provided. When the shoes care device 1 is provided with the pair of drying modules DM, one of the drying modules DM may form a 'drying module A (DM1)' as a drying module of the first management device 2*a*, and the other may form a 'drying module B (DM2)' as a drying module of the second management device 2*b*.

The 'drying module' described in one embodiment of the present invention may be understood to refer to each of the 'drying module A' and the 'drying module B' except as otherwise particularly limited.

In the shoes care device 1 according to one embodiment of the present invention, the drying module A (DM1) and the drying module B (DM2) may operate in different modes. When the drying module A (DM1) operates in a moisture absorption mode, the drying module B (DM2) may operate in a regeneration mode. Conversely, when the drying module A (DM1) operates in the regeneration mode, the drying module B (DM2) may operate in the moisture absorption mode.

The 'moisture absorption mode' described in the present invention means a case in which the dehumidifying part 330 adsorbs moisture in the air, and the 'regeneration mode' means a case in which the moisture adsorbed to the dehumidifying part 330 is separated by heating the dehumidifying part 330.

Naturally, both the drying module A (DM1) and the drying module B (DM2) may operate in the moisture absorption mode or may operate in the regeneration mode.

The module housing 200 may be fixedly coupled to a lower side of the inner cabinet 100. The module housing 200 may be detachably coupled to a lower side of the inner cabinet 100.

The module housing 200 includes the module chamber 210 that is a space having other components accommodated inside. That is, the module chamber 210 is a space inside the module housing 200 distinguished from an external space of the module housing 200. As described above, the module housing 200 forms part of the connection path F10, and accordingly, the module chamber 210 is configured to communicate with a space outside the module housing 200. The module chamber 210 communicates with the accommodation space 101 of the inner cabinet 100.

The module housing 200 may include a module case 201 and a module cover 202.

The module case 201 and the module cover 202 may be formed by injection molding, respectively, and may be assembled with each other after manufacturing to form the module housing 200.

The module case 201 is formed in the form of a container that is concave substantially downwards, and forms the module chamber 210 of the module housing 200.

The module case 201 may be configured in the form of a container opened upwards, and includes a module opening 201*a*.

In a plan view, an area of the module opening 201*a* may be larger than or equal to an area of the module chamber 210.

The module chamber 210 may include a first module chamber 212, a second module chamber 213, and a third module chamber 214. The module chamber 210 may include a suction module chamber 211.

In order to distinguish between the suction module chamber 211, the first module chamber 212, the second module chamber 213, and the third module chamber 214, a module partition wall 220 may be formed inside the module housing 200. Furthermore, the module partition wall 220 guides the movement of air so that air moves in a predetermined direction inside the module housing 200.

The suction module chamber 211 is a first space where air is introduced into the module housing 200.

The first module chamber 212 is a space in which the blowing part 310 is accommodated, the second module chamber 213 is a space in which the heating part 320 is accommodated, and the third module chamber 214 is a space in which the dehumidifying part 330 is accommodated.

In one embodiment of the present invention, the suction module chamber 211, the first module chamber 212, the second module chamber 213, and the third module chamber 214 may be formed at different positions in a plan view.

In addition, the air of the module chamber 210 may be configured to move through the suction module chamber 211, the first module chamber 212, the second module chamber 213, and the third module chamber 214 sequentially. That is, when the blowing part 310 is driven, air moves sequentially through the suction module chamber 211, the first module chamber 212, the second module chamber 213, and the third module chamber 214 inside the module housing 200.

The module case 201 may include a dry air outlet 231 and a wet air outlet 232.

The dry air outlet 231 may be formed in a hole shape opened to allow air in the third module chamber 214 to flow out. The dry air outlet 231 is formed adjacent to the third module chamber 214. The dry air outlet 231 may be formed on one edge of the module case 201. Furthermore, the dry air outlet 231 may be connected to the accommodation space 101 through the dry air duct 370 and the nozzle duct 810.

The wet air outlet 232 may be formed in a hole shape opened to allow the air in the third module chamber 214 to flow out. The wet air outlet 232 is formed adjacent to the third module chamber 214. The wet air outlet 232 may be formed on a frame on one side of the module case 201. Furthermore, the wet air outlet 232 may be connected to the condenser 400.

The dry air outlet 231 and the wet air outlet 232 may be formed adjacent to each other. The dry air outlet 231 and the wet air outlet 232 may be formed adjacent to any one vertex part of the module housing 200.

The suction module chamber 211 is formed adjacent to the first module chamber 212, and a bottom surface of the suction module chamber 211 may be inclined downwardly toward the first module chamber 212. Accordingly, air introduced into the suction module chamber 211 may naturally move toward the first module chamber 212 by hitting the bottom surface of the suction module chamber 211 forming an inclined surface, and a condensed water introduced into the suction module chamber 211 may move along the bottom surface of the suction module chamber 211 forming the inclined surface, and may move to the first module chamber 212.

The blowing part 310 may be assembled to the module housing 200 while being spaced apart from a bottom surface of the first module chamber 212. Furthermore, in this case, the blowing part 310 may be configured such that air may be introduced from a lower side of the first module chamber 212 to an interior of the blowing part 310 inside the first module chamber 212.

The module case 201 may include a first condensed water discharge hole 233.

The first condensed water discharge hole 233 is formed in a hole shape penetrating the module case 201. The first condensed water discharge hole 233 is formed on an edge of the module case 201 adjacent to a condenser 400 and formed to be equal to or lower than the bottom surface of the first module chamber 212, and communicates with the condenser 400. Among the bottom surfaces of the first module chamber 212, the first condensed water discharge hole 233 may form the lowest part, or the bottom surface of the first module chamber 212 may be formed such that a height thereof is lowered toward or at least equal to the first condensed water discharge hole 233.

As such, the first condensed water discharge hole 233 may be lower than the bottom surface of the first module chamber 212, and accordingly, the condensed water introduced into the first condensed water discharge hole 232 may move toward the first condensed water discharge hole 233 and flow into the condenser 400 through the first condensed water discharge hole 233.

Meanwhile, since the first condensed water discharge hole 233 is a hole in which the module housing 200 and the condenser 400 communicate with each other, the air inside the condenser 400 may flow into the module housing 200 through the first condensed water discharge hole 233. The air introduced into the module housing 200 through the first condensed water discharge hole 233 from an interior of the condenser 400 may move along the first module chamber 212, the second module chamber 213, and the third module chamber 214 by an operation of the blowing part 310 and may be introduced again into the condenser 400 and condensed.

The shoes care device 1 according to one embodiment of the present invention includes the condenser 400 coupled to an outer surface of the inner cabinet 100 and forming a regeneration path F20. In a plan view, the first module chamber 212 may be provided between the second module chamber 213 and the condenser 400. Since the first module chamber 212 is disposed between the second module chamber 213 and the condenser 400, a direct heat exchange between the condenser 400 and the heating part 320 is blocked, and the heat may be prevented from being transferred to the condenser 400 when the heating part 320 is heated inside the second module chamber 213.

Accordingly, when the dehumidifying part 330 is regenerated, condensation depending on heating of air by the heater 321 of the heating part 320 and cooling of air inside the condenser 400 may be effective performed.

The dehumidifying part 330 may be coupled to the module housing 200 while being spaced apart from a bottom surface of the third module chamber 214. Furthermore, in this case, the air inside the third module chamber 214 may move downwards through the dehumidifying part 330 from an upper side of the third module chamber 214.

The module case 201 may include a second condensed water discharge hole 234.

The second condensed water discharge hole 234 is formed in a hole shape penetrating the module case 201. The second condensed water discharge hole 234 is formed on the edge of the module case 201 adjacent to the condenser 400 and formed to be equal to or lower than the bottom surface of the third module chamber 214, and communicates with the condenser 400. Among the bottom surfaces of the third module chamber 214, the second condensed water discharge hole 234 may form the lowest part, or the bottom surface of the third module chamber 214 may be formed such that a height thereof is lowered toward or at least equal to the second condensed water discharge hole 234.

The second condensed water discharge hole 234 may be formed adjacent to the wet air outlet 232.

In this way, the second condensed water discharge hole 234 may be lower than the bottom surface of the third module chamber 214, and accordingly, condensed water introduced into the third module chamber 214 may move toward the second condensed water discharge hole 234, and may flow into the condenser 400 through the second condensed water discharge hole 234.

Meanwhile, since the second condensed water discharge hole 234 is a hole in which the module housing 200 and the condenser 400 communicate with each other, the air inside the condenser 400 may flow into the module housing 200 through the second condensed water discharge hole 234. In this way, the air introduced from the interior of the condenser 400 into the module housing 200 through the second condensed water discharge hole 234 moves directly to the wet air outlet 232 by the driving of the blowing part 310, and may be introduced again into the condenser 400 and condensed.

The module housing 200 may include the module cover 202.

The module cover 202 is coupled to the module case 201 while shielding the module opening 201*a* from an upper side of the module case 201. The module cover 202 may be detachably coupled to the module case 201. A plurality of locking projections 292 may protrude from one of the module cover 202 and the module case 201, and a plurality of locking grooves 291 into which the locking projections 292 are inserted and locked may be formed on the other. The locking projections 292 and locking grooves 291 are provided in a plural form, respectively, and may be spaced apart along an edge of the module housing 200 and repeatedly formed.

With the blowing part 310, the heating part 320, and the dehumidifying part 330 accommodated in the module case 201, the module cover 202 may shield the blowing part 310, the heating part 320, and the dehumidifying part 330 and may be coupled to the module case 201.

The shoes care device according to one embodiment of the present invention may be formed in a structure in which the dehumidifying part 330 may be detachable from the module housing 200. The structure of the shoes care device provides an advantage in maintaining and managing the dehumidifying part 330 and the shoes care device 1 on the whole.

On the other hand, the dehumidifying part 330 may be repeatedly used by regeneration, but with the repeated use, the dehumidifying part 330 needs to be replaced.

Considering these descriptions, the shoes care device 1 according to one specific embodiment of the present invention may be configured to separate and replace the dehumidifying part 330.

In one embodiment of the present invention, the module cover 202 of the module housing 200 may form a bottom surface of the inner cabinet 100.

The module cover 202 may form a boundary surface between the inner cabinet 100 and the module housing 200. The module cover 202 may be formed in a substantially rectangular shape.

The module cover 202 may be configured in substantially parallel with the horizontal direction.

Alternatively, the module cover 202 may be inclined to any one side. In one embodiment, an upper surface of the module cover 202 may be inclined downwardly toward the first direction (X direction) (a front side of the shoes care device 1).

In one embodiment of the present invention, the main shelf 40 is mounted in close contact with an upper side surface of the module cover 202, and the main shelf 40 mounted on the upper side surface of the module cover 202 is also configured to be inclined when the upper side surface of the module cover 202 is inclined. In this case, since an upper surface of the main shelf 40 is inclined, water (e.g., condensed water) placed on the upper surface of the main shelf 40 may flow along an inclined direction.

The shoes care device 1 may include a dehumidifying material cover 241.

The dehumidifying material cover 241 forms part of the module cover 202 that is the bottom of the inner cabinet 100. Furthermore, the dehumidifying material cover 241 may be detached from the module cover 202 of the inner cabinet 100 or may be hinge-coupled to the module cover 202.

In the module cover 202, a dehumidifying material exit 240 which is an opening of a shape and a size corresponding to the dehumidifying material cover 241 may be formed. The dehumidifying material cover 241 may be configured to open and close the dehumidifying material exit 240. The dehumidifying material cover 241 may be tightly coupled to the dehumidifying material exit 240. At least a part of the dehumidifying material cover 241 may be separated from the module cover 202. In one embodiment, the dehumidifying material exit 240 of the module cover 202 may be opened while completely separating the dehumidifying material cover 241 from the module cover 202, and in another embodiment, the dehumidifying material cover 241 of the module cover 202 may be opened while rotating the dehumidifying material cover 241 around a hinge axis. The dehumidifying part 330 may be introduced into or withdrawn from the module housing 200 through the dehumidifying material exit 240.

The dehumidifying material exit 240 and the dehumidifying material cover 241 may be formed in a position corresponding to the third module chamber 214 in a plan view. That is, the dehumidifying material exit 240 and the dehumidifying material cover 241 may be formed directly above the third module chamber 214. The shoes care device 1 according to one embodiment of the present invention may be configured such that the first module chamber 212 and the second module chamber 213 are not exposed in a plan view in a state where the dehumidifier cover 241 is opened.

When the dehumidifying material cover 241 is opened in the module cover 202, the third module chamber 214 disposed on a lower part of the module cover 202 is exposed through the dehumidifying material exit 240 of the module cover 202, and the dehumidifying part 330 may be settled inside the module case 201, or may be immediately withdrawn and separated from the module case 201.

The sizes and shapes of the dehumidifying material cover 241 and the dehumidifying material exit 240 are variously provided within the range capable of withdrawing or inserting the dehumidifying part 330.

The dehumidifying material cover 241 may be formed in a rectangular plate shape.

The length of the dehumidifying material cover 241 in the first direction (X direction) may be equal to or longer than the length of the dehumidifying part 330, and the length of the dehumidifying material cover 241 in the second direction (Y direction) may be equal to or longer than the length of the dehumidifying part 330.

As described above, in the shoes care device 1 according to one embodiment of the present invention, the heating part 320 and the dehumidifying part 330 are formed at different positions in a top plane view, and when the dehumidifying material cover 241 is opened on the module cover 202 that forms the bottom surface of the inner cabinet 100, the dehumidifying part 330 disposed directly below the dehumidifying material cover 241 may be withdrawn from the module housing 200, and the dehumidifying part 330 may be easily replaced by the user.

In addition, since only the third module chamber 214 is exposed in a state in which the dehumidifier cover 241 is opened, and the first module chamber 212 and the second module chamber 213 are not exposed, the blowing part 310 accommodated in the first module chamber 212 and the heating part 320 accommodated in the second module chamber 213 are not exposed. That is, since the blowing part 310 and the heating part 320 are not directly exposed to the user, safety accidents due to an unintended operation of the blowing part 310 and/or the heating part 320 can be prevented.

The dehumidifying material cover 241 may be configured to separately shield the dehumidifying part 330. A space between the dehumidifying material cover 241 and the dehumidifying part 330 may form a part of the connection path F10.

As described above, the outlet 203 forms an inlet through which the air inside the inner cabinet 100 is sucked into the module housing 200. The outlet 203 may form a start part of the connection path F10. The outlet 203 may be formed in the shape of a hole vertically penetrated from the bottom surface (the upper surface of the module cover 202) of the inner cabinet 100.

A network such as a grid shape, a mesh shape, etc., may be formed on the outlet 203.

The outlet 203 may be formed parallel to the second direction (Y direction). That is, the outlet 203 may be formed in a long hole shape in the module cover 202 along the second direction (Y direction).

The outlet 203 may be formed on an edge of the module cover 202. The outlet 203 may be formed on the edge of the module cover 202 along the second direction (Y direction).

The outlet 203 may be formed on a front part or a rear part of the module cover 202 based on the first direction (X direction).

The outlet 203 may be disposed relatively close to the door 30 in the module cover 202. That is, the outlet 203 may be disposed relatively in the front of the module cover 202.

The upper surface of the module cover 202 may be inclined downwardly toward the outlet 203. That is, a part of the module cover 202 where the outlet 203 is formed may be configured to be the lowest. Accordingly, when water is present on the module cover 202 or the main shelf 40, such water may flow along the surface of the module cover 202 by gravity and flow into the inlet 203.

In the shoes care device 1 according to one embodiment of the present invention, the module chamber 210 is provided inside the module housing 200, and the module chamber 210 includes a first module chamber 212, a second module chamber 213, and the third module chamber 214. The first module chamber 212, the second module chamber 213, and the third module chamber 214 may be formed at different positions in a plan view. That is, the blowing part 310, the heating part 320, and the dehumidifying part 330 may be disposed at different positions in the module housing 200. According to one embodiment of the present invention, the blowing part 310, the heating part 320, and the dehumidifying part 330, which are main means for drying the air inside the inner cabinet 100 and main means for regenerating the dehumidifying part 330, are disposed together in the module chamber 210 of the module housing 200. Accordingly, the blowing part 310, the heating part 320, and the dehumidifying part 330 are disposed at positions considerably close to each other.

In one embodiment of the present invention, the module case 201 of the module housing 200 may be integrally formed by injection molding. In this case, the bottom parts of the module housing 200 may be integrally formed, the bottom parts may not be assembled with each other, and no gaps may be formed in the bottom parts.

In the arrangement explained above, the condensed water can be effectively prevented from leaking from the module housing 200. In addition, a vertical height of the module housing 200 can be minimized.

When moisture remains at an unintended part inside the shoes care device 1, such moisture may reproduce bacteria or cause odors. This is why there is need for countermeasures to solve the problems, and the shoes care device 1 according to one embodiment of the present invention can effectively prevent water from leaking in consideration of such problems.

In the shoes care device 1 according to one embodiment of the present invention, the air in the module chamber 210 may sequentially move the first module chamber 212, the second module chamber 213, and the third module chamber 214. Accordingly, since the third module chamber 214 and a drying flow path F10*b* may be connected in the shortest distance, which provides excellent drying efficiency by the dehumidifying part 330, and air heated by the heating part 320 moves directly to the dehumidifying part 330 to form the shoes care device 1 with excellent regeneration efficiency.

In the shoes care device 1 according to one embodiment of the present invention, the module housing 200 includes the suction module chamber 211, and the bottom surface of the suction module chamber 211 may be inclined downwardly toward the first module chamber 212. Accordingly, the air introduced through the outlet 203 moves naturally to the first module chamber 212 by hitting the bottom surface of the suction module chamber 211, and the condensed water introduced into the outlet 203 moves to the first module chamber 212 such that the condensed water can be easily drained.

The shoes care device 1 according to one embodiment of the present invention may include the condenser 400, and the module case 201 may include the first condensed water discharge hole 233. In addition, the module case 201 may include the second condensed water discharge hole 234. Accordingly, the dehumidifying part 330 may be effectively regenerated, and condensed water inside the module housing 200 may be easily discharged to the condenser 400.

In the shoes care device 1 according to one embodiment of the present invention, steam generated by the steam generator 700 is supplied to the accommodation space 101 of the inner cabinet 100, and to this end, the shoes care device 1 includes a steam inlet 204.

The steam inlet 204 forms an inlet through which steam is supplied to the accommodation space 101 of the inner cabinet 100.

In the shoes care device according to one embodiment of the present invention, the steam inlet 204 is formed in the module housing 200.

The steam inlet 204 may be formed in a rear part of the module housing 200 based on the first direction (X direction). The steam inlet 204 may be formed to vertically penetrate the module housing 200. The steam inlet 204 may be formed to vertically penetrate the module case 201 and the module cover 202. The steam inlet 204 may be formed in the center in a right-left direction at the rear part of the module housing 200.

The steam inlet 204 may be formed on a rear edge of the module housing 200, and may be formed directly behind a position where the third module chamber 214 is formed. The third module chamber 214 and the steam inlet 204 are shielded from each other.

In the module housing 200, the module cover 202 forms the bottom surface of the accommodation space 101, and when the module housing 200 is coupled to the inner cabinet 100, the steam inlet 204 is formed behind the bottom of the inner cabinet 100.

The steam generator 700 and the steam valve 710 are disposed in a lower part, the distance from the steam generator 710 to the steam inlet 204 can be reduced by forming the module housing 200, and the steam inlet 204 in a rear part of the module housing 200, and an increase in the load required for the supply of steam can be prevented. Accordingly, steam may be smoothly supplied from the steam generator 700 to the steam inlet 204.

Figure 11:
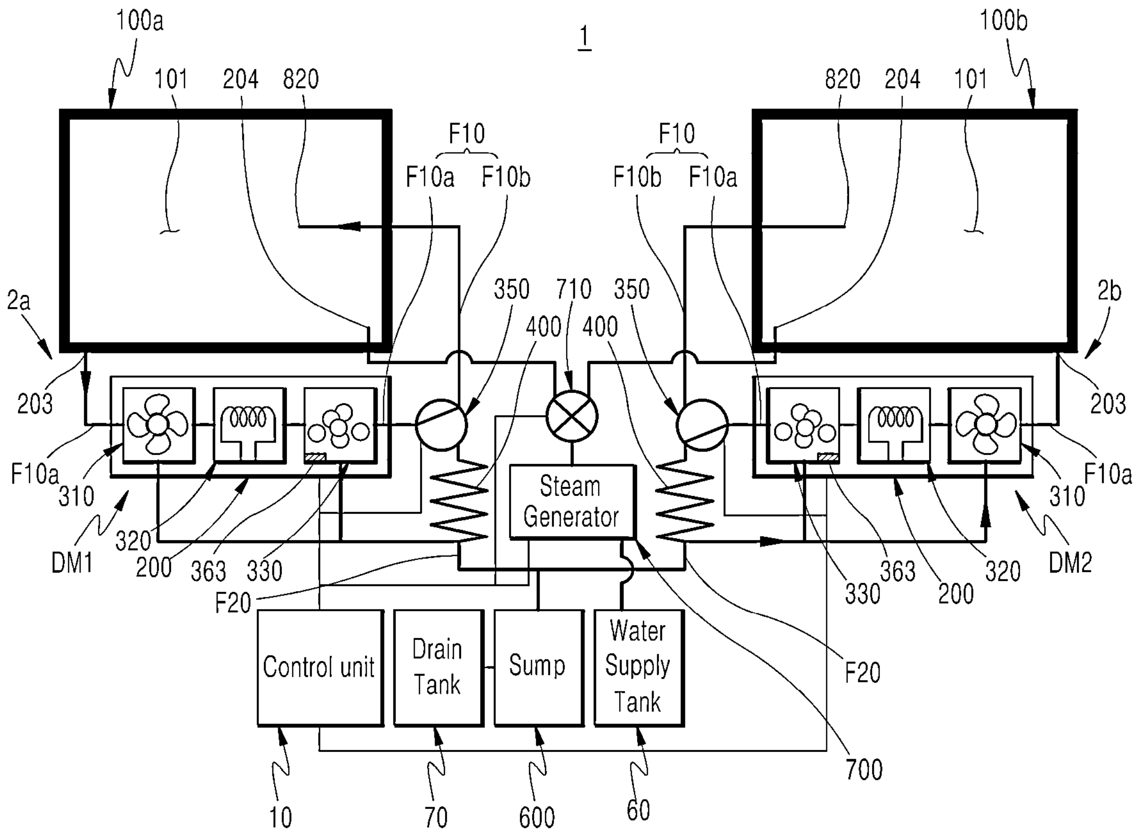
FIG. 11 is a diagram illustrating a connection relationship between components and a flow of fluid in the shoes care device according to one embodiment of the present invention.

FIG. 11 is a diagram illustrating a connection relationship between components and a flow of fluid in the shoes care device 1 according to one embodiment of the present invention.

The connection path F10 forms a movement path of air connected from the outlet 203 to the nozzle 820. That is, the outlet 203 may form an inlet of the connection path F10, and the nozzle 820 may form an outlet of the connection path F10.

The outlet 203 may be coupled to communicate with the inner cabinet 100, and the nozzle 820 may be provided inside the inner cabinet 100. Except the outlet 203 and the nozzle 820, one part of the connection path F10 may be provided inside the inner cabinet 100, and the other part may be provided outside the inner cabinet 100.

The air inside the inner cabinet 100 moves to the connection path F10 through the outlet 203, and the air passing through the connection path F10 moves back into the inner cabinet 100 through the nozzle 820. As such air flow is repeated, the air circulation is performed in the shoes care device 1.

In the nozzle 820, a hole through which air is discharged is formed in the accommodation space 101 of the inner cabinet 100, and the nozzle 820 may form a last part of the connection path F10.

In the shoes care device 1 according to one embodiment of the present invention, since the nozzle 820 is configured to be movable to various positions inside the inner cabinet 100, the shoes may be managed in various positions.

As described above, the dehumidifying part 330 is disposed in the connection path F10. The air moving through the connection path F10 passes through the dehumidifying part 330, and the dehumidifying part 330 absorbs moisture from the air moving through the connection path F10 such that the air from which moisture has been removed may be supplied into the inner cabinet 100.

The connection path F10 may be divided into a conversion flow path F10*a* and a drying flow path F10*b*. The conversion flow path F10*a* and the drying flow path F10*b* form a movement path of air sequentially connected to each other. The air in the connection path F10 may sequentially move through the conversion flow path F10*a* and the drying flow path F10*b*.

The conversion flow path F10*a* forms an upstream section of the connection path F10, which is connected to the outlet 203. The conversion flow path F10*a* may be a section in which the blowing part 310, the heating part 320, and the dehumidifying part 330 are disposed. The conversion flow path F10*a* may be formed by the module housing 200, and the module chamber 210 inside the module housing 200 may form the conversion flow path F10*a*.

The conversion flow path F10*a* may be a section in which humid air moves and dries. The conversion flow path F10*a* may be a section in which air is dehumidified by the dehumidifying part 330.

Meanwhile, the conversion flow path F10*a* may be a section in which the dehumidifying part 330 (the dehumidifying material 331) are regenerated.

The drying flow path F10*b* forms a downstream section of the connection path F10, which connects the conversion flow path F10*a* to the nozzle 820. A flow path formed by the drying air duct 370, the nozzle duct 810, and the nozzle 820 may form the drying flow path F10*b*.

The drying passage F10*b* may be a section in which dry air with moisture removed therefrom moves.

When the drying module DM operates in the moisture absorption mode, the drying flow path F10*b* communicates with the conversion flow path F10*a*, and when the drying module DM operates in the regeneration mode, the drying flow path F10*b* and the conversion flow path F10*a* may not communicate with each other such that the drying flow path F10*b* and the conversion flow path F10*a* block each other.

Accordingly, when air is dehumidified by the dehumidifying part 330 in the conversion flow path F10*a*, the dried air moves through the drying flow path F10*b*.

The dry air duct 370 may be fixedly coupled to an outer wall surface of the inner cabinet 100, and the nozzle duct 810 may be provided inside the inner cabinet 100.

As the dry air duct 370 is tightly coupled to an inner rear plate 110 of the inner cabinet 100, a flow path may be formed between the dry air duct 370 and the inner cabinet 100 (the inner rear plate 110), and such a flow path may form a part of the drying flow path F10*b*. A lower part of the dry air duct 370 communicates with the dry air outlet 231 of the module housing 200, an upper part thereof communicates with the nozzle duct 810, which connect the interior of the module housing 200 and the interior of the nozzle duct 810 for mutual communication.

As described above, after humid air in the accommodation space 101 of the inner cabinet 100 flows into the conversion flow path F10*a*, the air is dehumidified by the dehumidifying part 330 and converted into dry air, and the dry air can be resupplied to the accommodation space 101 of the inner cabinet 100 through the drying flow path F10*b*.

The regeneration path F20 forms a movement path of a fluid.

The regeneration path F20 forms a passage through which air and/or condensed water inside the shoes care device moves.

The regeneration path F20 forms a path through which air and/or condensed water passing through the dehumidifying part 330 moves when the dehumidifying material 331 is regenerated. The regeneration path F20 may be entirely or partially formed of a pipe, a hose, a tube, a duct, a housing, or a combination thereof.

Moisture generated during the regeneration process of the dehumidifying material 331 needs to be discharged through a separate flow path separated from the drying flow path F10*b*, which is a flow path through which dry air moves. Accordingly, the shoes care device 1 according to one embodiment of the present invention includes the regeneration path F20, and when the dehumidifying material 331 is regenerated, air passing through the dehumidifying part 330 is not ventilated to the nozzle 820 but moves through the regeneration path F20.

The regeneration path F20 is a flow path branched from the connection path F10. The regeneration path F20 may be branched from the connection path F10 to form a path different from that of the drying flow path F10*b* of the connection path F10. The regeneration path F20 is connected to the sump 600.

The regeneration path F20 may be a section that connects the conversion flow path F10*a* and the sump 600.

The regeneration path F20 may be a section in which humid air separated from the dehumidifying part 330 moves.

The condenser 400 according to one embodiment of the present invention forms a regeneration path F20. Moisture separated from the dehumidifying material 331 may be condensed after moving to the condenser 400 along with air moving along the regeneration path F20. In addition, condensed water condensed in the condenser 400 may be moved to the sump 600 through the regeneration path F20, collected from a lower part of the sump 600, and then discharged to the drain tank 70, discharged to the outside, or pressed to the steam generator 700.

In the shoes care device 1 according to one embodiment of the present invention, when the drying module DM operates in the regeneration mode, the regeneration path F20 communicates with the conversion flow path F10*a*, and when the drying module DM operates in the moisture absorption mode, the regeneration path F20 and the conversion flow path F10 may not communicate with each other such that the regeneration path F20 and the conversion flow path F10 block each other.

Accordingly, when the dehumidifying part 330 is regenerated in the conversion flow path F10*a*, humid air containing moisture separated from the dehumidifying part 330 moves through the regeneration path F20.

In one embodiment of the present invention, the damper 350 may be formed in the form of a damper valve.

The damper 350 may be rotatably coupled to the module housing 200. The damper 350 may be coupled to the module housing 200 in a form accommodated in the module housing 200.

As described above, in the module housing 200, the dry air outlet 231 forming an inlet of the drying flow path F10*b* is formed as a passage of the connection path F10, and the wet air outlet 232 forming an inlet of the regeneration path F20 is formed.

The damper 350 controls a movement path of air passing through the dehumidifying material 331 in the module housing 200. Depending on the operation of the damper 350, the air passing through the dehumidifying material 331 may move into the inner cabinet 100 through the nozzle 820 or may move into the regeneration path F20.

The damper 350 may be configured to open the regeneration path F20 while blocking the drying flow path F10*b*, or to open the drying flow path F10*b* while blocking the regeneration path F20.

The damper 350 may be configured to selectively shield the dry air outlet 231 and the wet air outlet 232. The damper 350 may be configured to selectively seal the dry air outlet 231 and the wet air outlet 232.

The damper 350 may selectively block one of the dry air outlet 231 and the wet air outlet 232. When the damper 350 opens the dry air outlet 231 while blocking the wet air outlet 232, the air passing through the dehumidifying material 331 may move into the inner cabinet 100 through the nozzle 820, and when the damper 350 opens the wet air outlet 232 while blocking the dry air outlet 231, the air passing through the dehumidifying material 331 may be condensed while moving through the regeneration path F20.

In the shoes care device 1 according to one embodiment of the present invention, the damper 350 may be configured to be hinge-rotatable around a hinge axis 350*a* formed on one side. The hinge axis 350*a* of the damper 350 may be parallel to the third direction (Z direction). In addition, the shoes care device 1 may include a damper motor 351 configured to rotate the damper 350 around the hinge axis 350*a* of the damper 350. The damper motor 351 may be formed as an electric motor and may be configured to rotate the damper 350 bidirectionally.

When the damper 350 opens the dry air outlet 231 and seals the wet air outlet 232, the air inside the inner cabinet 100 moves along the connection path F10 and is circulated by sequentially passing through the inlet 203, the module housing 200 (the blowing part 310 and the dehumidifying part 330, the dry air outlet 231, the dry air duct 370, the nozzle duct 810, and the nozzle 820.

When the damper 350 seals the dry air outlet 231 and opens the wet air outlet 232, the air moves along the conversion flow path F10*a* and the regeneration path F20 and is circulated by sequentially passing through the module housing 200 (the blowing part 310, the heating part 310, and the dehumidifying part 330), the wet air outlet 232, and the condenser 400.

In one embodiment of the present invention, the controller 10 may control the damper motor 351 such that the damper 350 closes the dry air outlet 231 and opens the wet air outlet 232 when the heating part 320 is turned on. In addition, the controller 10 may control the damper motor 351 such that the damper 350 opens the dry air outlet 231 and closes the wet air outlet 232 when the heating part 320 is turned off.

Accordingly, by controlling the damper motor 351 by the controller 10, the damper 350 may open the drying flow path F10*b* and close the regeneration path F20 when the heating part 320 is turned off, and may close the drying flow path F10*b* and open the regeneration path F20 when the heating part 320 is turned on.

The damper motor 351 may be controlled individually in each of the first management device 2*a* and the second management device 2*b*.

Referring to FIG. 11, in the drying module A (DM1) of the first management device 2*a*, the damper 350 seals the wet air outlet 232 and opens the dry air outlet 231 of the second management device 2*b*, and in the drying module B (DM2) of the second management device 2*b*, when the damper 350 opens the wet air outlet 232 and seals the dry air outlet 231, the air in the conversion flow path F10*a* of the first management device 2*a* may flow through the drying flow path F10*b*, and the air in the conversion flow path F10*a* of the second management device 2*b* may flow through the regeneration path F20. Furthermore, in this case, the drying module A (DM1) of the first management device 2*a* may operate in the moisture absorption mode, and the drying module B (DM2) of the second management device 2*b* may operate in the regeneration mode.

In contrast, when in the drying module A (DM1) of the first management device 2*a*, the damper 350 opens the wet air outlet 232 and seals the dry air outlet 231, and in the drying module B (DM2) of the second management device 2*b*, the damper 350 seals the wet air outlet 232 and opens the dry air outlet 231, the air in the conversion flow path F10*a* of the first management device 2*a* may flow along the regeneration path F20, and the air in the conversion flow path F10*a* of the second management device 2*b* may flow along the drying flow path F10*b*. Furthermore, in this case, the drying module A (DM1) of the first management device 2*a* may operate in the regeneration mode, and the drying module B (DM2) of the second management device 2*b* may operate in the moisture absorption mode.

In both the drying module A (DM1) of the first management device 2*a* and the drying module B (DM2) of the second management device 2*b*, when the damper 350 seals the wet air outlet 232 and opens the dry air outlet 231, both the drying module A (DM1) and the drying module B (DM2) may operate in the moisture absorption mode.

In both the drying module A (DM1) of the first management device 2*a* and the drying module B (DM2) of the second management device 2*b*, when the damper 350 seals the dry air outlet 231 and opens the wet air outlet 232, both the drying module A (DM1) and the drying module B (DM2) may operate in the regeneration mode.

In the shoes care device 1 according to one embodiment of the present invention, the first management device 2*a* and the second management device 2*b* individually include the inner cabinet 100, the connection path F10, the blowing part 310, and the dehumidifying part 330. In addition, the shoes care device 1 includes the steam generator 700 and the steam valve 710. Accordingly, the degree of the supply of steam, the degree of dehumidification by the dehumidifying part 330, and the flow of air circulated along the connection path F10 may be different in each of the first management device 2*a* and the second management device 2*b*, and the first management device 2*a* and the second management device 2*b* may manage shoes under different conditions.

In addition, the first management device 2*a* and the second management device 2*b* include the module housing 200, the blowing part 310, the heating part 320, the dehumidifying part 330, and the drying flow path F10*b*, respectively. The air and condensed water moving in the first management device 2*a* and the air and condensed water moving in the second management device 2*b* move along different paths, thereby achieving accurate control intended in each of the first management device 2*a* and the second management device 2*b*. In this case, since the first management device 2*a* and the second management device 2*b* share and use the steam generator 700, the steam generator 700 can be efficiently utilized in the shoes care device 1, and the shoes care device 1 can efficiently utilize the space.

In addition, as described above, when the shoes are dried in one of the first management device 2*a* and the second management device 2*b*, the dehumidifying part 330 may be regenerated in the other, and the efficient management of the shoes and efficient use of the shoes care device 1 can be achieved.

In the shoes care device 1 according to one embodiment of the present invention, the first management device 2*a* and the second management device 2*b* each include the regeneration path F20 and the damper 350 individually.

The controller 10 may control the heating part 320 (the heater 321) and the damper 350 to interwork with each other.

The controller 10 may control the damper 350 to open the drying flow path F10*b* and close the regeneration path F20 when the heating part 320 is turned off, and may control the damper 350 to close the drying flow path F10*b* and open the regeneration path F20 when the heating part 320 is turned on.

The controller 10 may control each component of the shoes care device 1 such that air flowing into the module chamber 210 from the accommodation space 101 and passing through the dehumidifying part 330 moves along the drying flow path F10*b* when the heating part 320 is turned off (when the heater 321 of the heating part 320 is turned off), and the air moves along the regeneration path F20 when the heating part 320 is turned on (when the heater 321 of the heating part 320 is turned on).

Such control may be performed individually in each of the first management device 2*a* and the second management device 2*b*. Accordingly, since the movement path of air inside the module chamber 210 is changed depending on an operation of the heating part 320, the drying of the shoes and the regeneration of the dehumidifying part 330 can be effectively achieved.

The controller 10 may control the steam valve 710 and the heating part 320 to interwork with each other.

The controller 10 may control the steam valve 710 such that when the heating part 320 of the first management device 2*a* is turned off, the valve disk 715 closes or opens the first valve outlet 713, when the heating part 320 of the first management device 2*a* is turned on, the valve disk 715 closes the first valve outlet 713, when the heating part 320 of the second management device 2*b* is turned off, the valve disk 715 closes or opens the second valve outlet 714, and when the heating part 320 of the second management device 2*b* is turned on, the valve disk 715 closes the second valve outlet 714.

In this way, the supply of steam to the accommodation space 101 of the inner cabinet 100 and the operation of the heating part 320 inside the module housing 200 may interwork with each other to effectively perform the drying of the shoes and the regeneration of the dehumidifying part 330.

The shoes care device 1 according to one embodiment of the present invention may include a first sensor 361 and a second sensor 362 (see FIG. 9).

The first sensor 361 may be installed in the second module chamber 213 of the module housing 200, and the second sensor 362 may be installed in the third module chamber 214 of the module housing 200. The first sensor 361 may be configured to measure the temperature and/or humidity of the second module chamber 213, and the second sensor 362 may measure the temperature and/or humidity of the third module chamber 214.

The first sensor 361 measures the temperature and/or humidity of air before passing through the dehumidifying part 330, and the second sensor 362 measures the temperature and/or humidity of air after passing through the dehumidifying part 330.

The controller 10 may compare the temperature and/or humidity of the second module chamber 213 measured by the first sensor 361 with the temperature and/or humidity of the third module chamber 214 measured by the second sensor 362 to recognize a state and a change of the temperature and/or humidity inside the module housing, and may also check an operation state of the drying module DM.

The controller 10 may recognize the temperature and humidity of the second module chamber 213 measured by the first sensor 361, and the temperature and humidity of the third module chamber 214 measured by the second sensor 362 to recognize a change in the humidity inside the module housing 200. Accordingly, the degree of dehumidification by the dehumidifying part 330 may be checked, and the degree of regeneration of the dehumidifying part 330 may be checked.

In one embodiment, when the drying module DM operates in the moisture absorption mode, the controller 10 may control the drying module DM to stop operating in the moisture absorption mode and operate in the regeneration mode if a humidity change amount of the second module chamber 213 recognized by the first sensor 361 and a humidity change amount of the third module chamber 214 recognized by the second sensor 362 is less than or equal to a reference value.

In one embodiment, when the drying module DM operates in the regeneration mode, the controller 10 may control the drying module DM to stop operating in the regeneration mode if the humidity change amount of the second module chamber 213 recognized by the first sensor 361 and the humidity change amount of the third module chamber 214 recognized by the second sensor 362 is less than or equal to the reference value.

The shoes care device 1 according to one embodiment of the present invention further includes a third sensor 363 capable of measuring the amount of moisture adsorbed to the dehumidifying material 331, and the controller 10 may control the drying module DM to operate the regeneration mode until the amount of moisture measured by the third sensor 363 is less than or equal to a set value.

Specifically, the controller 10 may control all the heating parts 320 to operate until the amount of moisture measured by the third sensor 363 is less than or equal to the set value.

In this case, as illustrated in FIG. 11, the third sensor 363 may include a moisture sensor installed adjacent to the dehumidifying material 331 to measure the amount of moisture adsorbed to the dehumidifying material 331, and the type and number thereof may vary as necessary.

In this way, when the moisture adsorbed on the dehumidifying material 331 is sensed to exceed the reference value, the shoes care device 1 according to one embodiment of the present invention first regenerates all dehumidifying materials 331 until the moisture is less than or equal to the reference value. Accordingly, the dehumidifying material 331 can maintain an appropriate state for dehumidification all the time even when the shoes care device 1 operates to refresh the shoes.

Figure 12:
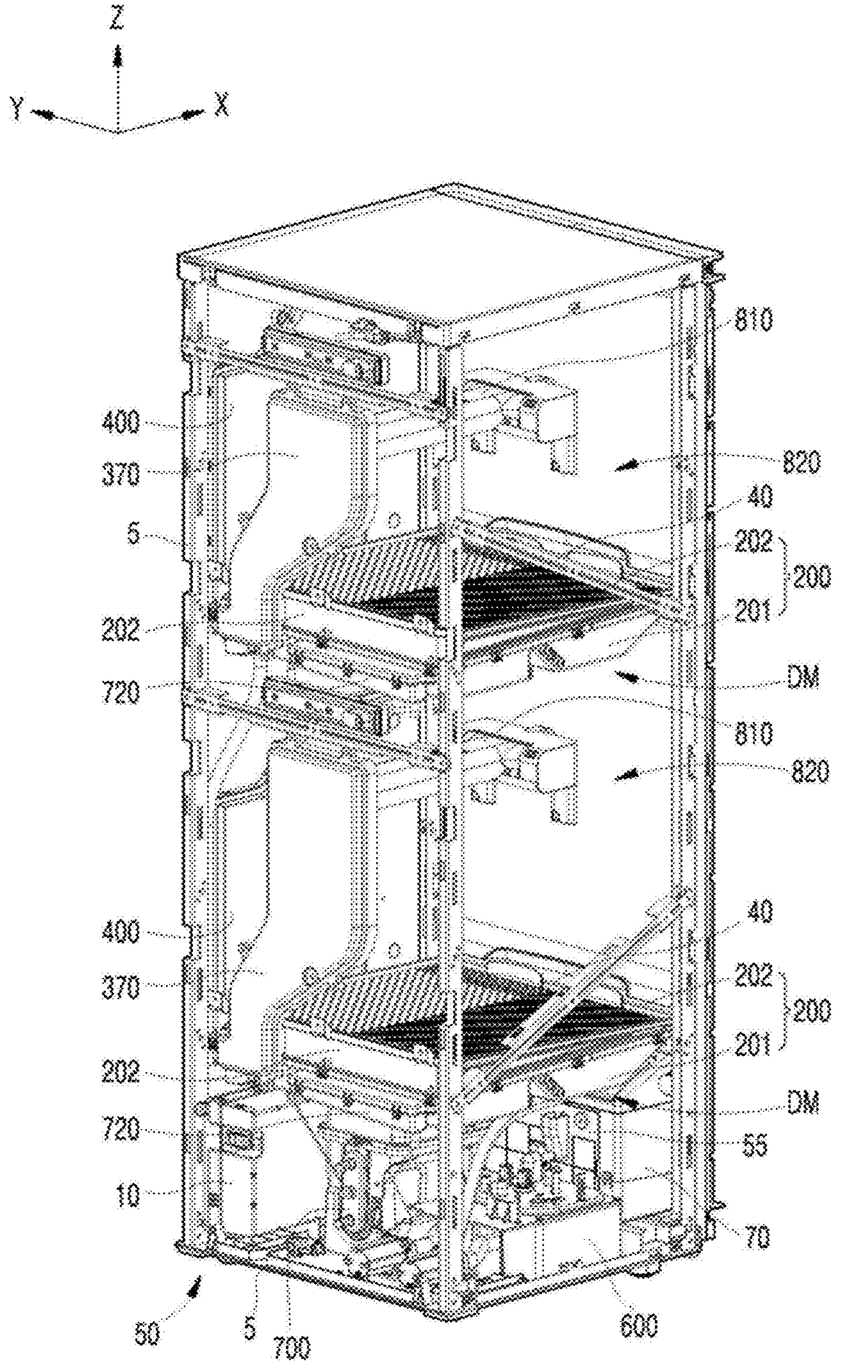
FIG. 12 is a perspective view illustrating a modified example of a state in which the door, the outer cabinet, and the inner cabinet are removed from the shoes care device according to one embodiment of the present invention.
Figure 13:
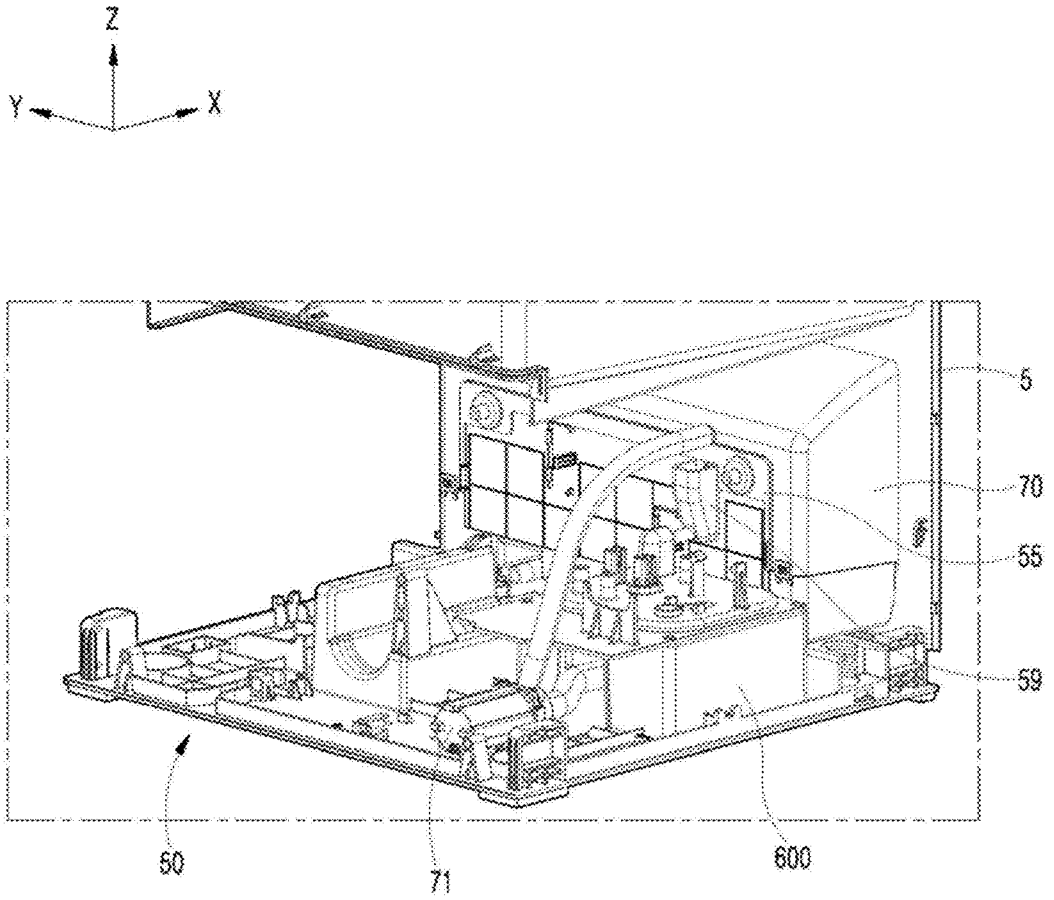
FIG. 13 is a perspective view illustrating a part of the machine room of the shoes care device illustrated in FIG. 12.
Figure 14:
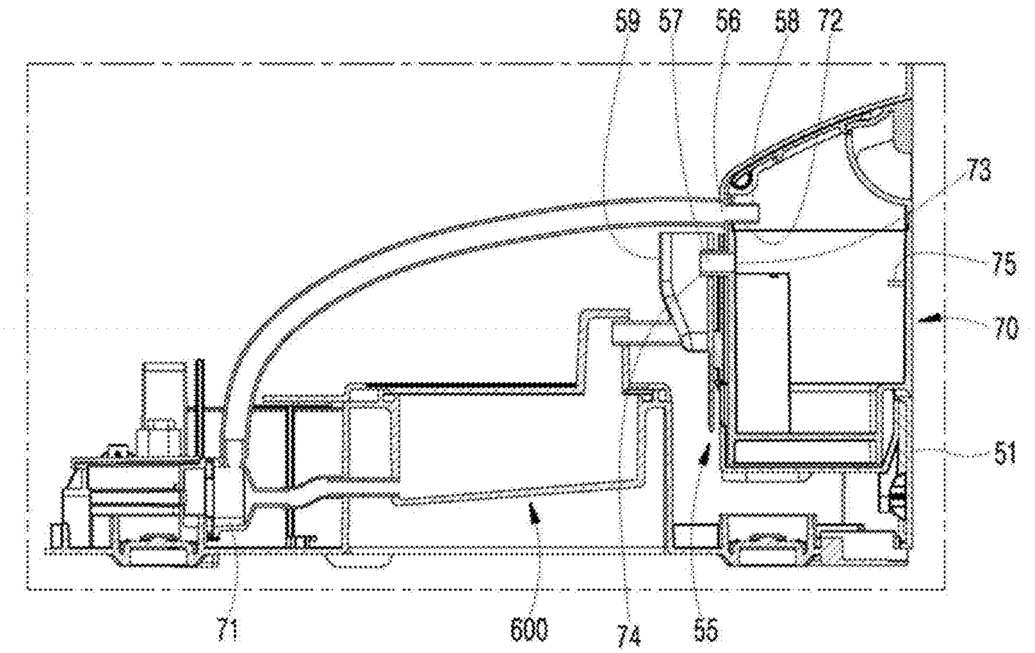
FIG. 14 is a cross-sectional view illustrating a sump and a drain tank in more detail in a part of the machine room of the shoes care device illustrated in FIG. 12.
Figure 15:
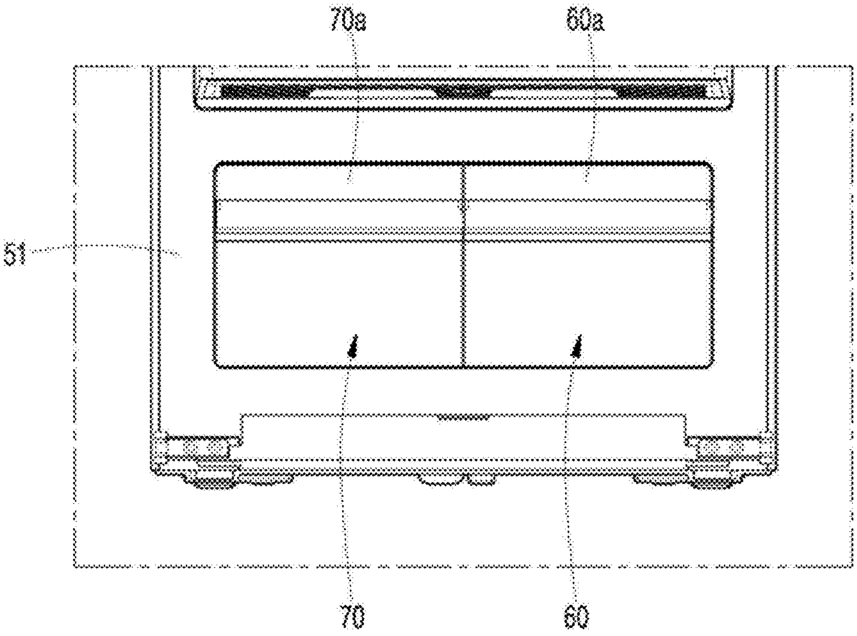
FIG. 15 is a view illustrating a front surface of a machine room in the shoes care device according to one embodiment of the present invention.
Figure 16:
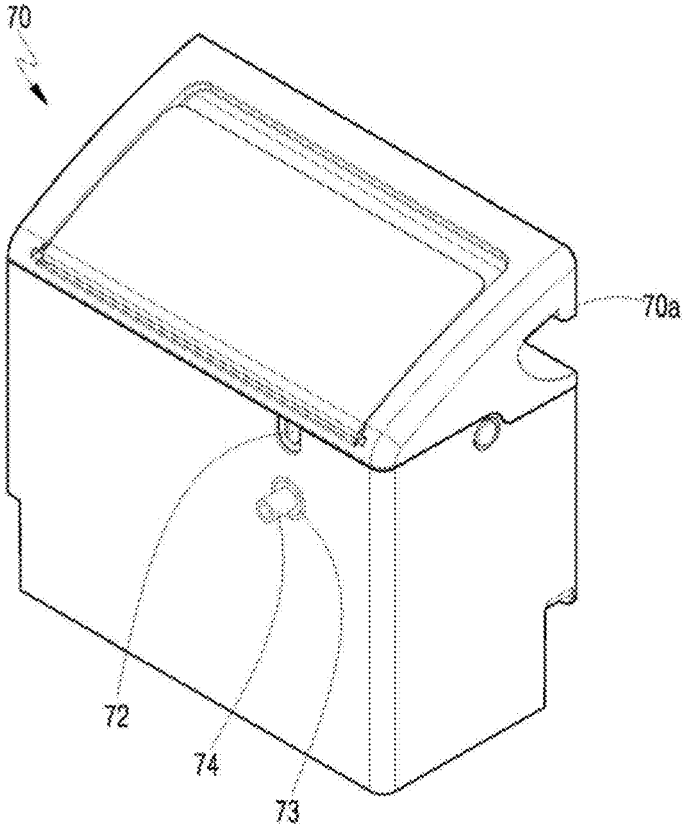
FIG. 16 is a perspective view illustrating the drain tank in more detail in the shoes care device according to one embodiment of the present invention.
Figure 17:
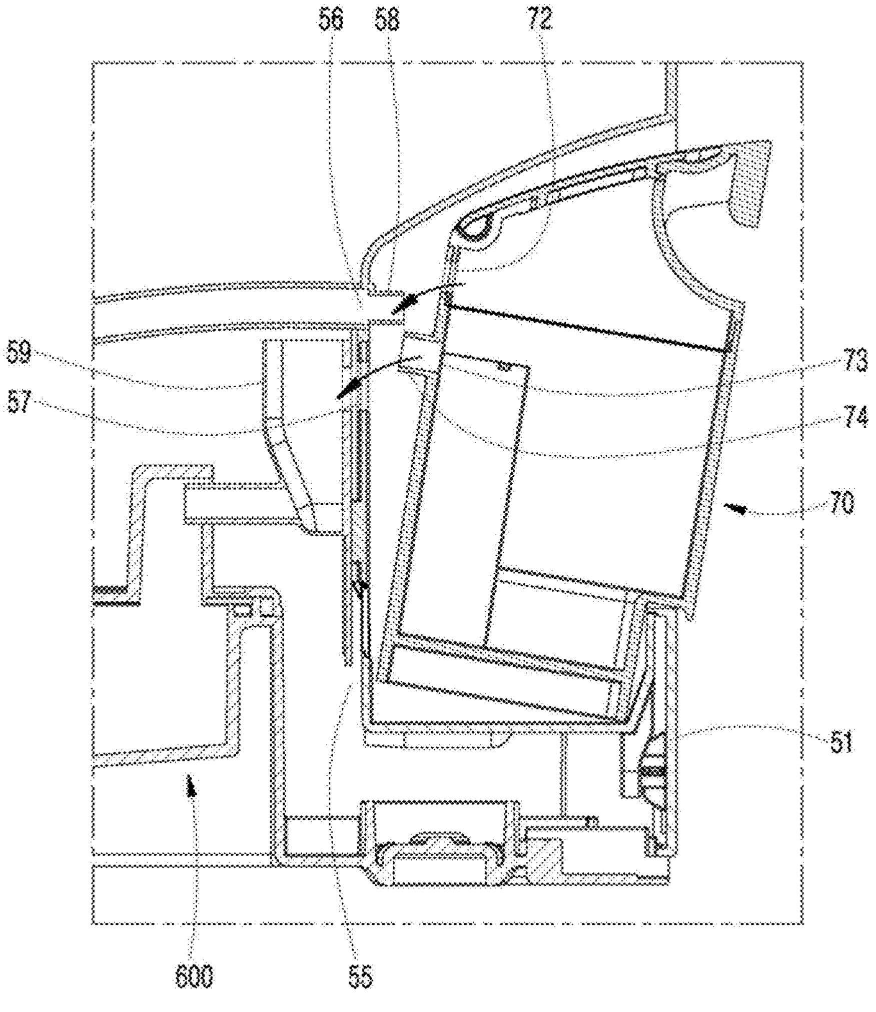
FIG. 17 is a view exemplarily illustrating a detachable state of the drain tank in the shoes care device according to one embodiment of the present invention.

FIG. 12 is a perspective view illustrating a modified example of a state in which the door 30, the outer cabinet 20, and the inner cabinet 100 are removed from the shoes care device 1 according to one embodiment of the present invention. FIG. 13 is a perspective view illustrating a part of the machine room 50 of the shoes care device 1 illustrated in FIG. 12. FIG. 14 is a cross-sectional view illustrating the sump 600 and the drain tank 70 in more detail in the part of the machine room 50 of the shoes care device 1 illustrated in FIG. 12. FIG. 15 is a view illustrating a front surface of the machine room 50 in the shoes care device 1 according to one embodiment of the present invention. FIG. 16 is a perspective view illustrating the drain tank 70 in more detail in the shoes care device 1 according to one embodiment of the present invention. FIG. 17 is a view exemplarily illustrating a detachable state of the drain tank 70 in the shoes care device 1 according to one embodiment of the present invention.

The shoes care device 1 according to one embodiment of the present invention may include the inner cabinet 100, the connection path F10, the blowing part 310, a dehumidifying part 330, the heating part 320, the regeneration path F20, the sump 600, and the drain tank 70. In this case, the drain tank 70 may include a first drain inlet hole 72 and a first water level limit hole 73.

The inner cabinet 100 is a part in which an accommodation space 101 for accommodating the shoes is formed, and the outlet 203 and a nozzle 820 may be disposed inside.

The connection path F10 forms a flow path through which air from the accommodation space 101 is discharged from the inner cabinet 100 and then introduced back into the accommodation space 101, and the air inside the inner cabinet 100 is absorbed to the module chamber 210 and ventilated and is dehumidified in the process of passing through the dehumidifying part 330.

The blowing part 310 is a part disposed in the connection path F10 and configured to ventilate air, and may inhale air from the inner cabinet 100 by the operation of the blowing part 310 and ventilate the inhaled air from the connection path F10.

The dehumidifying part 330 is a part disposed in the connection path F10 and configured to dehumidify air, and with the heating of the dehumidifying material 331, the dehumidifying material 331 may be regenerated in a state where moisture adsorbed on the dehumidifying material 331 is separated to perform a dehumidifying function.

The heating part 320 is a part disposed in the connection path F10 and configured to heat air, and the dehumidifying part 330 may be heated by heating the air supplied to a dehumidifying material portion.

The regeneration path F20 is a flow path formed to allow the air heated by the heating part 320 to move and branched from the connection path F10, and may form a passage through which air and/or condensed water through the dehumidifying part 330 moves.

The module chamber 210 is a part configured to ventilate air from the accommodation space 101, disposed on a path of air through which the dehumidifying part 330 is ventilated and capable of heating the dehumidifying part 330.

In this case, with the heating of the dehumidifying part 330, the dehumidifying part 330 may be generated in a state where the moisture adsorbed to the dehumidifying part 330 is separated to perform the dehumidifying function.

To this end, the module chamber 210 may include the dehumidifying part 330, the blowing part 310, the heating part 320, the damper 350, etc.

Specifically, the module chamber 210 may form a part of the regeneration path F20 branched and ventilated from the connection path F10 in which air circulates between the outlet 203 and the nozzle 820 and the connection path F10 passing through the dehumidifying part 330.

Accordingly, the air in the accommodation space 101 may move to the connection path F10 or the regeneration path F20 while the air is ventilated to the module chamber 210 to pass through the dehumidifying part 330.

The controller 10 is a part that controls the shoes care device 1, and control the module chamber 210 to selectively open and close the connection path F10 and the regeneration path F20 depending on whether the dehumidifying part 330 is heated.

That is, the controller 10 may selectively open and close the connection path F10 and the regeneration path F20 depending on whether the dehumidifying part 330 is regenerated.

The connection path F10 is a part where air is circulated between the outlet 203 and the nozzle 820, and the outlet 203 may form an inlet of the connection path F10, and the nozzle 820 may form an outlet of the connection path F10.

That is, the connection path F10 may be an air flow path of a path through which the air inside the inner cabinet 100 is dehumidified while being sucked and ventilated into the module chamber 210 to pass through the dehumidifying part 330 and is supplied back into the inner cabinet 100.

As described above, the shoes care device 1 according to one embodiment of the present invention can not only collect moisture and bacteria in the air ventilated by placing the dehumidifier 330 in the module chamber 210 but also heat and regenerate the dehumidifying part 330, thus appropriately maintaining the performance for a shoes treatment all the time.

In addition, the shoes care device 1 according to one embodiment of the present invention can form the connection path F10 through which air circulates between the outlet 203 and the nozzle 820 respectively disposed inside the inner cabinet 100, thus preventing the air used for dehumidification and deodorization of shoes from being exposed to the user.

The sump 600 has a structure capable of accommodating water. The sump 600 is configured to accommodate condensed water generated by the shoes care device 1 inside. The sump 600 is configured to receive the condensed water condensed in the condenser 400.

In this case, the condensed water collected in the sump 600 may be moved to the drain tank 70 through a separate pipe, etc., may be immediately discharged to the outside of the shoes care device 1, or may be reused in another component.

The drain tank 70 may be configured to store water discharged from the shoes care device 1 inside. The drain tank 70 may store water condensed inside the shoes care device 1. The drain tank 70 may be configured to store water drained from the sump 600.

The first drain inlet hole 72 is a part formed in an upper end such that the water drained from the sump 600 may be introduced, and may be a passage through which water flows into the drain tank 70. Since the first drain inlet hole 72 is formed in an upper end of the drain tank 70, water may be accommodated inside the drain tank 70 up to the height at which the first drain inlet hole 72 is formed.

However, when water is accommodated in the drain tank 70 above the height at which the first drain inlet hole 72 is formed, the water may flow to the outside of the drain tank 70. Specifically, when water flows into the drain tank 70 to a height close to the height at which the first drain inlet hole 72 is formed, the water may overflow when the drain tank 70 shakes or tilts. Accordingly, a water level needs to be appropriately adjusted at a height lower than the height at which the first drain inlet hole 72 is formed.

Accordingly, it is necessary for the user to confirm that the water is accommodated at a predetermined level or higher inside the drain tank 70 and discharge the water accommodated in the drain tank 70.

However, since the user's carelessness or difficulty in confirming an inner level of the drain tank 70 causes the water not to be appropriately discharged, the water may flow to the outside of the drain tank 70 and then overflow.

In this case, since the water overflowing outside the drain tank 70 may leak into an unintended part, the function of each component of the shoes care device 1 may be degraded, or problems of contamination and bacterial growth may occur.

Accordingly, when the water is accommodated in the drain tank 70 at a predetermined height or more, the water level inside the drain tank 70 needs to be appropriately regulated by introducing the water back into the sump 600.

To this end, the first water level limit hole 73 is a part formed in a lower part of the first drain inlet hole 72 and connected to the sump 600, and when the water level inside the drain tank 70 reaches the height at which the first drain inlet hole 72 is formed, water may be reintroduced into the sump 600.

That is, as illustrated in FIG. 14, the water flowing into the drain tank 70 through the first drain inlet hole 72 may be accommodated in the drain tank 70 up to the height at which the first drain inlet hole 72 is formed. Further, when the water level inside the drain tank 70 reaches the height at which the first drain inlet hole 72 is formed, the water may be discharged through the first drain inlet hole 72 and the water level inside the drain tank 70 may not exceed the height at which the first drain inlet hole 72 is formed.

In this way, in the shoes care device 1 according to one embodiment of the present invention, since the first water level limit hole 73 connected to the sump 600 is formed in a lower part of the first drain inlet hole 72 connected again to the sump 600 and allowing the water to flow into the drain hole 70, water above a water level that can be accommodated in the drain tank 70 may be discharged to the sump 600. This can prevent leakage to an unintended part in the process of discharging water through the drain tank 70.

The shoes care device 1 according to one embodiment of the present invention may further include the machine room 50 provided in the lower side of the inner cabinet 100, and the sump 600 and the drain tank 70 may be disposed in the machine room 50.

That is, as illustrated in FIGS. 12 and 13, the machine room 50 may be provided in the lower side of the inner cabinet 100 to accommodate some components constituting the shoes care device 1. In this case, the components accommodated in the machine room 50 may be fixed to the main frame 5 or may be fixed to the inner cabinet 100 or the inner cabinet 20.

In this case, the inner cabinet 100 and the machine room 50 may form separate spaces inside the shoes care device 1. Further, the controller 10, the sump 600, the steam generator 700, and the steam valve 710 may be accommodated in the machine room 50. Furthermore, the machine room 50 may be configured to accommodate the water supply tank 60 and the drain tank 70.

Accordingly, since the inner cabinet 100 may form a space that mainly accommodates the articles (the shoes S) to be managed, only the minimum components necessary for functionality is placed inside.

In this way, in the shoes care device 1 according to one embodiment of the present disclosure, since the sump 600 and the drain tank 70 are disposed in the machine room 50 below the inner cabinet 100, water can be discharged naturally from the shoes care device 1 in a downward direction, and the components arranged in the inner cabinet 100 can be minimized.

The shoes care device 1 according to one embodiment of the present invention further includes a water pump 71 that presses the water drained from the sump 600 to the first drain inlet hole 72, and the sump 600 may be installed on a bottom surface of the machine room 50.

That is, as illustrated in FIGS. 12 to 14, a water pump (a second water pump 71) may be connected to the drain tank 70 to discharge water from the sump 600 to the drain tank 70. The drain tank 70 and the second water pump 71 may be connected by a pipe, a hose, etc.

According to the pressing of water through the water pump 71, there is no need for the drain tank 70 to be disposed lower than the sump 600. That is, even if the sump 600 is disposed lower than the drain tank 70, water may be smoothly discharged from the sump 600 to the drain tank 70.

Meanwhile, the sump 600 for accommodating the condensed water on a water discharge path is preferably disposed at the lowest part in the shoes care device 1. In this case, the drain tank 70 may be preferably placed at the lowest part in the shoes care device 1. However, given that the user has to frequently check the level of the drain tank 70 and discharge the water from the drain tank 70 to the outside in some cases, there may be some limitations in arranging the drain tank 70 in a low position.

Therefore, the sump 600 is disposed in the lowest position in the shoes care device 1, and when the drain tank 70 is disposed in a higher position than the sump 600, water is discharged smoothly through the pressing of the water pump 71.

As described above, since the shoes care device 1 according to one embodiment of the present invention presses water from the sump 600 installed on the bottom surface of the machine room 50 and moves the pressed water to the drain tank 70, the sump 600 that accommodates the condensed water inside the shoes care device 1 can be disposed in the lowest position and drained smoothly.

In the shoes care device 1 according to one embodiment of the present invention, the drain tank 70 may be installed on the first wall 51 formed on the front surface of the machine room 50 and exposed to the outside of the first wall 51.

Specifically, as illustrated in FIG. 15, the machine room 50 may include the first wall 51. In that case, the first wall 51 may form the front wall surface of the machine room 50.

The first wall 51 may be erected in the vertical direction or may be erected in a substantially vertical direction. In one embodiment, the first wall 51 may form a wall surface orthogonal to or inclined with the first direction (X direction).

The drain tank 70 may be coupled to the machine room 50 to get exposed from the outside of one wall surface of the machine room 50. Specifically, the drain tank 70 may be disposed in front of the machine room 50.

The drain tank 70 may form one wall surface of the machine room 50 along with the first wall 51. When the first wall 51 forms the front surface of the machine room 50, the drain tank 70 may be exposed from the front of the machine room 50 and may be coupled to the machine room 50 to get exposed from the outside of the first wall 51.

In this way, in the shoes care device 1 according to one embodiment of the present invention, since the drain tank 70 is exposed outwards from the first wall 51 on the front surface of the machine room 50, the drain tank 70 can be easily checked even if the user does not check the inside of the machine room 50.

In the shoes care device 1 according to one embodiment of the present invention, the drain tank 70 may be detachably installed on the first wall 51.

That is, as illustrated in FIG. 17, the drain tank 70 may be separated from the machine room 50 in an outward direction of the first wall 51. In this case, for the easy attachment and detachment of the drain tank 70, the handle 70*a* of the drain tank 70 may be formed on the outer surface of the drain tank 70.

Accordingly, when the water stored in the drain tank 70 needs to be removed, the user may separate the drain tank 70 from the first wall 51 and then discard the water. In addition, even if the drain tank 70 needs to be cleaned or inspected and replaced, a predetermined operation can be performed after separating the drain tank 70 from the first wall 51.

In this way, in the shoes care device 1 according to one embodiment of the present invention, since the drain tank 70 is detached from the first wall 51 on the front surface of the machine room 50, the water stored in the drain tank 70 can be easily discharged and the drain tank 70 can be easily managed.

In the shoes care device 1 according to one embodiment of the present invention, the drain tank 70 may be accommodated in an accommodation housing 55 formed to be recessed from the first wall 51 to the inside of the machine room 50.

That is, as illustrated in FIGS. 14 and 17, the accommodation housing 55 may be coupled to the rear of the first wall 51 of the machine room 50. The accommodation housing 55 may be formed to surround a lower surface and a rear surface of the drain tank 70 to support the drain tank 70 mounted on the first wall 51.

Specifically, since the accommodation housing 55 covers the rear of the first wall 51 while separating the drain tank 70, the inside of the machine room 50 can be exposed at a minimum in the front of the shores care device 1.

As described above, in the shoes care device 1 according to one embodiment of the present invention, since the accommodation housing 55 for accommodating the drain tank 70 is formed from the first wall 51 to the inside of the machine room 50, the drain tank 70 can be installed more stably, and the inside of the machine room 50 can be exposed at a minimum even when the drain tank 70 is separated.

In the shoes care device 1 according to one embodiment of the present invention, the accommodation housing 55 may include a second drain inlet hole 56 formed in an upper end of the rear surface thereof and connectable to the first drain inlet hole 72, and a second water level limit hole 57 formed under the second drain inlet hole 56 and connectable to the first water level limit hole 73.

That is, as illustrated in FIGS. 14 and 17, the second drain inlet hole 56 formed in the accommodation housing 55 may be connected to the first drain inlet hole 72 formed in the drain tank 70 to form a passage through which water flows from the sump 600 to the drain tank 70.

In addition, the second water level limit hole 57 formed in the accommodation housing 55 may be connected to the first water level limit hole 73 formed in the drain tank 70 to form a passage through which water flows back into the sump 600.

As described above, in the shoes care device 1 according to one embodiment of the present invention, since the second drain inlet hole 56 and the second water level limit hole 57 are formed in the accommodation housing 55, the drain tank 70 accommodated in the accommodation housing 55 can be smoothly connected to the sump 600.

In the shoes care device 1 according to one embodiment of the present invention, the accommodation housing 55 may further include a drain inlet 58 protruding from the second drain inlet hole 56 and inserted into the first drain inlet hole 72, and the drain tank 70 may further include a water level limit pipe 74 protruding from the first water level limit hole 73 and inserted into the second water level limit hole 57.

That is, a drain inlet pipe 58 may protrude from the second drain inlet hole 56 and be inserted into the first drain inlet hole 72. Furthermore, the water level limit pipe 74 may protrude from the first water level limit hole 73 and be inserted into the second water level limit hole 57.

Accordingly, when the drain tank 70 is mounted in the accommodation housing 55, the drain inlet pipe 58 can be easily inserted into the first drain inlet hole 72, and the water level limit pipe 74 can be easily inserted into the second water level limit hole 57.

That is, as illustrated in FIG. 17, the user mounts the drain tank 70 in the accommodation housing 55 from the front surface of the machine room 50 while the drain tank 70 is partially inclined.

In this case, when both the drain inlet pipe 58 and the water level limit pipe 74 protrude from the accommodation housing 55, in the inclined drain tank 70, it may be difficult for the first drain inlet hole 72 and the first water level limit hole 73 to be arranged in the drain inlet pipe 58 and the water level limit pipe 74.

Conversely, even if both the drain inlet pipe 58 and the water level limit pipe 74 protrude from the drain tank 70, in the inclined drain tank 70, it may be difficult for the drain inlet pipe 58 and the water level limit pipe 74 to be arranged with the second drain inlet hole 56 and the second water level limit hole 57.

Accordingly, as the drain inlet pipe 58 and the water level limit pipe 74 is made to protrude piece by piece in the accommodation housing 55 and the drain tank 70, respectively, the drain tank 70 needs to be easily detached from the accommodation housing 55.

In the shoes care device 1 according to one embodiment of the present invention described above, since the drain inlet pipe 58 protrudes from the second drain inlet hole 56 and the water level limit pipe 74 protrudes from the first water level limit hole 73, the drain tank 70 can be easily detached from the accommodation housing 55.

In the shoes care device 1 according to one embodiment of the present invention, the accommodation housing 55 may cover a rear side of the second water level limit hole 57 to accommodate water discharged from the second water level limit hole 57, and may further include a connection cover 59 connected to the sump 600.

That is, as illustrated in FIG. 14, the water discharged through the second water level limit hole 57 may not directly flow into the sump 600, and a part thereof may be temporarily accommodated in the connection cover 59.

In this case, since the inside of the connection cover 59 has a predetermined space, water may be partially accommodated by the volume of the corresponding space. At the same time, since water may flow to the sump 600 through a lower part of the connection cover 59, the water reintroduced from the drain tank 70 to the sump 600 may not move rapidly, but may be partially buffered and moved from the connection cover 59.

As described above, in the shoes care device 1 according to one embodiment of the present invention, since the connection cover 59 receives the water discharged from the second water level limit hole 57 and transmits the water to the sump 600, a buffer space for water reintroduced from the drain tank 70 to the sump 600 may be partially formed.

In the shoes care device 1 according to one embodiment of the present invention, a part of the upper surface of the sump 600 may protrude upwards, and the connection cover 59 may be connected to a protruding part of the upper surface of the sump 600.

That is, since the lower part of the connection cover 59 is arranged with the protruding part of the upper surface of the sump 600, water may be moved from the connection cover 59 to the sump 600 through the corresponding part.

As described above, the sump 600 and the drain tank 70 may have different arrangement heights, and in particular, when the sump 600 is disposed on the bottom surface of the machine room 50, the drain tank 70 may be disposed higher than the sump 600.

Accordingly, in order to facilitate the movement of water reintroduced from the drain tank 70 to the sump 600, a protruding part may be formed on the upper surface of the sump 600 at a height corresponding to the lower part of the connection cover 59.

Specifically, as illustrated in FIGS. 13 and 14, when the lower part of the connection cover 59 is assembled with the protruding part of the upper surface of the sump 600, a separate pipe is not required to improve convenience and structural simplicity.

As described above, in the shoes care device 1 according to one embodiment of the present invention, since a part of the upper surface of the sump 600 protrudes and is connected to the connection cover 59, the accommodation housing 55 and the sump 600 can be more easily coupled to each other.

The shoes care device 1 according to one embodiment of the present invention may further include a water level sensor 75 installed to sense a level of water stored in the drain tank 70.

That is, the water level sensor 75 is installed inside the drain tank 70 to sense the level of water stored in the drain tank 70. Further, when the water level sensed by the water level sensor 75 reaches a set height, the user can recognize that the drain tank 70 needs to be managed by informing the user of this state.

In this case, the water level sensor 75 may include a magnetic sensor etc., but the present invention is not limited thereto, and the water level sensor 75 may include various components for sensing the water level.

On the other hand, when the water level sensor 75 does not operate normally due to malfunctioning, etc., a certain amount of water may be restricted by allowing water to flow back from the drain tank 70 to the sump 600 as described above.

In addition, when the water flows back from the drain tank 70 to the sump 600 and the water level capacity of the sump 600 reaches the limit, the operation of the shoes care device 1 may be controlled to stop due to a drainage error.

As described above, since the shoes care device 1 according to one embodiment of the present invention is provide with the water level sensor 75 that senses the water level inside the drain tank 70, it can be easily recognized whether the water needs to be discharged from the drain tank 70.

The shoes care device 1 according to one embodiment of the present invention further includes the condenser 400 that forms a part of the regeneration path F20, and allows air to be introduced and condensed along the regeneration path F20, and the condensed water condensed in the condenser 400 may be introduced and accommodated in the sump 600.

Specifically, the moisture separated from the dehumidifying part 330 may be condensed after moving to the condenser 400 with air moving along the regeneration path F20. In addition, the condensed water condensed in the condenser 400 may move to the sump 600 through the regeneration path F20, and may be collected from the lower part of the sump 600 and then discharged.

The condenser 400 may be configured to be entirely metallic. The condenser 400 may be made of a metal having excellent thermal conductivity. The condenser 400 may be made of aluminum.

As described above, since the shoes care device 1 according to one embodiment of the present invention includes the condenser 400 that generates condensed water on the regeneration path F20, moisture generated during the regeneration process of the dehumidifying part 330 may be condensed and accommodated in the sump 600.

In the shoes care device 1 according to one embodiment of the present invention, the condenser 400 may be disposed at a position relatively higher than the sump 600.

Accordingly, since the condensed water condensed inside the condenser 400 may flow into the sump 600 while being naturally lowered by gravity, stream can be effectively condensed and discharged when the dehumidifying material 331 is regenerated.

As described above, since the shoes care device 1 according to one embodiment of the present invention is configured to have a lower height from the condenser 400 to the sump 600, the condensed water can move smoothly between the condenser 400 and the sump 600.

The shoes care device 1 according to one embodiment of the present invention may further include the water supply tank 60 installed on the first wall 51 parallel to the drain tank 70 and exposed to the outside of the first wall 51.

Specifically, the water supply tank 60 may be configured to store water supplied into the shoes care device 1 inside. The water supply tank 60 may be configured to store water supplied to the steam generator 700.

In order to supply water from the water supply tank 60 into the shoes care device 1, the water pump 61 (the first water pump 61) may be connected to the water supply tank 60. The water supply tank 60 and the first water pump 61 may be connected by a pipe, a hose, etc.

Specifically, as illustrated in FIG. 15, the water supply tank 60 may form one wall surface of the machine room 50 along with the first wall 51. When the first wall 51 forms the front surface of the machine room 50, the water supply tank 60 may be exposed from the front of the machine room 50 and may be coupled to the machine room 50 to get exposed from the outside of the first wall 51.

In this way, in the shoes care device 1 according to one embodiment of the present invention, since the water supply tank 60 is exposed outwards from the first wall 51 on the front surface of the machine room 50, the water supply tank 60 can be easily checked even if the user does not check the inside of the machine room 50.

In the shoes care device 1 according to one embodiment of the present invention, the water supply tank 60 may be detachably installed on the first wall 51.

That is, the water supply tank 60 may be separated from the machine room 50 in the outer direction of the first wall 51. In this case, in order to facilitate the attachment and detachment of the water supply tank 60, the handle 60*a* of the water supply tank 60 may be formed on the outer surface of the water supply tank 60.

Accordingly, when water needs to be supplied to the water supply tank 60, the user may separate the water supply tank 60 from the first wall 51 and then fill the water supply tank 60 with water. In addition, even if the water supply tank 60 needs to be cleaned or inspected and replaced, the water supply tank 60 can be separated from the first wall 51, and a predetermined operation can be then performed.

In this way, in the shoes care device 1 according to one embodiment of the present invention, since the water supply tank 60 is detached from the first wall 51 on the front surface of the machine room 50, the water can be easily supplied to the water supply tank 60 and the water supply tank 60 can be easily managed.

Hereinabove, a specific embodiment of the present invention is described and illustrated, but the present invention is not limited to the disclosed embodiment, and it may be appreciated by those skilled in the art that the exemplary embodiment can be variously modified and transformed to another specific embodiment without departing from the spirit and the scope of the present invention. Therefore, the scope of the present invention will not be defined by the described embodiment, but defined by the technical spirit disclosed in the claims.

INDUSTRIAL APPLICABILITY

By at least one of exemplary embodiments of the present invention, a dehumidifying part is disposed in a module chamber not only to collect moisture and bacteria in a ventilation air but also to regenerate the dehumidifying part by heating the dehumidifying part in the module chamber, thereby maintaining proper shoes treatment performance all the time.

In addition, by at least one of exemplary embodiments of the present invention, a connection path through which air circulates is formed between an outlet and a nozzle respectively disposed inside an inner cabinet, thereby preventing the air used for dehumidifying and deodorizing shoes from being exposed to the user.

In addition, according to at least one of the embodiments of the present disclosure, since the first water level limit hole connected again to the sump is provided under the first drain inlet hole connected to the sump and allowing water to flow into the drain tank therethrough so that the water exceeding the water level that can be accommodated in the drain tank is discharged, water can be prevented from leaking to an unintended portion in the process of discharging water through the sump.

In addition, according to at least one of the embodiments of the present disclosure, since the sump and the drain tank are disposed in the machine room under the inner cabinet, water can be naturally discharged from the shoe care device downward, and the number of components disposed in the inner cabinet can be minimized.

In addition, according to at least one of the embodiments of the present disclosure, since water is pumped from the sump installed on the bottom surface of the machine room to the drain tank, smooth drainage can be achieved by disposing the sump that accommodates the water condensed inside the shoe care device at the lowest position.

In addition, according to at least one of the embodiments of the present disclosure, since the drain tank is exposed to the outside from the first wall of the front surface of the machine room, even if a user does not check the inside of the machine room, the drain tank can be easily checked.

In addition, according to at least one of the embodiments of the present disclosure, since the drain tank is detachable from the first wall of the front surface of the machine room, the water stored in the drain tank can be easily discharged, and the drain tank can be easily managed.

In addition, according to at least one of the embodiments of the present disclosure, since the accommodation housing in which the drain tank is accommodated is provided from the first wall toward the inside of the machine room, the drain tank can be installed more stably, and the exposure of the inside of the machine room can be minimized even when the drain tank is separated.

In addition, according to at least one of the embodiments of the present disclosure, since the second drain inlet hole and the second water level limit hole are provided in the accommodation housing, the drain tank and the sump accommodated in the accommodation housing can be smoothly connected.

In addition, according to at least one of the embodiments of the present disclosure, since the drain inlet pipe protrudes from the second drain inlet hole, and the water level limit pipe protrudes from the first water level limit hole, the drain tank can be easily attached and detached to and from the accommodation housing.

In addition, according to at least one of the embodiments of the present disclosure, since the connection cover receives water discharged from the second water level limit hole and delivers the water to the sump, a buffer space may be provided to a certain extent for water reintroduced into the sump from the drain tank.

In addition, according to at least one of the embodiments of the present disclosure, since a portion of the upper surface of the sump protrudes and is connected to the connection cover, the housing and the sump can be more easily coupled to each other.

In addition, according to at least one of the embodiments of the present disclosure, since the water level sensor is installed to detect the water level inside the drain tank, it can be easily determined whether or not water needs to be discharged from the drain tank.

In addition, according to at least one of the embodiments of the present disclosure, since the condenser that generates condensed water is included on the regeneration path, the moisture generated in the process of the regeneration by the dehumidifying part can be condensed and accommodated in the sump.

In addition, according to at least one of the embodiments of the present disclosure, since the height is configured to be reduced from the condenser to the sump, the condensed water can be smoothly moved between the condenser and the sump.

In addition, according to at least one of the embodiments of the present disclosure, since the water supply tank is exposed to the outside from the first wall of the front surface of the machine room, even if a user does not check the inside of the machine room, the water supply tank can be easily checked.

In addition, according to at least one of the embodiments of the present disclosure, since the drain tank is detachable from the first wall of the front surface of the machine room, water supply to the water supply tank and management of the water supply tank can be easily performed.

The invention claimed is:

1. A shoe care device comprising:

an accommodation space configured to accommodate shoes;

a connection path defining a flow path through which air in the accommodation space is introduced thereinto and then discharged therefrom into the accommodation space;

a blower located in the connection path, the blower being configured to blow the air;

a dehumidifier located in the connection path, the dehumidifier being configured to dehumidify the air;

a heater located in the connection path to heat the air;

a regeneration path branching from the connection path, the regeneration path being configured such that air heated by the heater moves therethrough;

a sump configured to accommodate water condensed inside the shoe care device; and a drain tank configured to store water drained from the sump, the drain tank including:

a first drain inlet hole located at an upper end of the drain tank, the first drain inlet hole being configured to receive the water drained from the sump; and a first water level limit hole located below the first drain inlet hole, the first water level limit hole being connected to the sump.

2. The shoe care device of claim 1, further comprising a machine room located at a lower side of the inner cabinet, wherein the sump and the drain tank are located in the machine room.

3. The shoe care device of claim 2, further comprising a water pump configured to pump the water drained from the sump to the first drain inlet hole, wherein the sump is located at a bottom surface of the machine room.

4. The shoe care device of claim 2, wherein the machine room includes a first wall defining a front surface of the machine room, and wherein the drain tank is located on the first wall, the drain tank being exposed outside the front surface of the machine room.

5. The shoe care device of claim 4, wherein the drain tank is removably attached to the first wall.

6. The shoe care device of claim 4, further comprising an accommodation housing recessed inward from the first wall and into the machine room, wherein the drain tank is accommodated in the accommodation housing.

7. The shoe care device of claim 6, wherein the accommodation housing comprises:

a second drain inlet hole located at an upper end of a rear surface of the accommodation housing, the second drain inlet hole being configured to connect to the first drain inlet hole; and a second water level limit hole located under the second drain inlet hole, the second water level limit hole being configured to connect to the first water level limit hole.

8. The shoe care device of claim 7, wherein the accommodation housing further comprises a drain inlet pipe protruding from the second drain inlet hole, the drain inlet pipe being configured to be inserted into the first drain inlet hole, and wherein the drain tank further comprises a water level limit pipe protruding from the first water level limit hole, the water level limit pipe being configured to be inserted into the second water level limit hole.

9. The shoe care device of claim 7, wherein the accommodation housing further comprises a connection cover configured to cover a rear side of the second water level limit hole, the connection cover being configured to receive water discharged from the second water level limit hole, the connection cover being connected to the sump at a lower end of the connection cover.

10. The shoe care device of claim 9, wherein a portion of an upper surface of the sump protrudes upward, and wherein the connection cover is connected to the portion of the upper surface of the sump.

11. The shoe care device of claim 4, further comprising a water supply tank located on the first wall adjacent the drain tank, the water tank being exposed outside the front surface of the machine room.

12. The shoe care device of claim 11, wherein the water supply tank is removably attached to the first wall.

13. The shoe care device of claim 11, further comprising:

a steam generator configured to generate steam to be introduced into the accommodation space; and a water pump configured to connect the water supply tank to the steam generator.

14. The shoe care device of claim 11, wherein the drain tank includes a handle located on an outer surface of the drain tank, and wherein the water supply tank includes a handle on an outer surface of the water supply tank.

15. The shoe care device of claim 11, wherein a front surface of the drain tank is coplanar with a front surface of the water supply tank.

16. The shoe care device of claim 1, further comprising a water level sensor located in the drain tank.

17. The shoe care device of claim 1, further comprising a condenser defining a portion of the regeneration path, the condenser being configured to condense water from the air introduced along the regeneration path, wherein the water condensed in the condenser is introduced into and accommodated in the sump.

18. The shoe care device of claim 17, wherein the condenser is located relatively higher than the sump.

19. A shoe care device comprising:

an accommodation space configured to accommodate shoes;

a connection path defining a flow path through which air in the accommodation space is introduced thereinto and then discharged therefrom into the accommodation space;

a blower located in the connection path, the blower being configured to blow the air;

a dehumidifier located in the connection path, the dehumidifier being configured to dehumidify the air;

a heater located in the connection path to heat the air;

a regeneration path branching from the connection path, the regeneration path being configured such that air heated by the heater moves therethrough;

a sump configured to accommodate water condensed inside the shoe care device;

a drain tank configured to store water drained from the sump, the drain tank being exposed through a front surface of the shoe care device; and a water supply tank adjacent to the drain tank, the water supply tank being exposed through the front surface of the shoe care device.

20. The shoe care device of claim 19, further comprising a machine room located at a lower side of the inner cabinet, wherein the sump, the drain tank, and the water supply tank are located in the machine room.

* * * * *